US008034899B2

(12) United States Patent
Dwyer et al.

(10) Patent No.: US 8,034,899 B2
(45) Date of Patent: *Oct. 11, 2011

(54) HIV FUSION INHIBITOR PEPTIDES WITH IMPROVED BIOLOGICAL PROPERTIES

(75) Inventors: John Dwyer, Chapel Hill, NC (US); Brian L. Bray, Graham, NC (US); Stephen E. Schneider, Raleigh, NC (US); Huyi Zhang, Durham, NC (US); Nicolai A. Tvermoes, Durham, NC (US); Barbara E. Johnston, Raleigh, NC (US); Paul E. Friedrich, Apex, NC (US)

(73) Assignee: Trimeris, Inc., Durham, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 12/254,259

(22) Filed: Oct. 20, 2008

(65) Prior Publication Data

US 2009/0105143 A1    Apr. 23, 2009

Related U.S. Application Data

(63) Continuation of application No. 11/701,910, filed on Feb. 2, 2007, now Pat. No. 7,456,251.

(60) Provisional application No. 60/764,674, filed on Feb. 2, 2006.

(51) Int. Cl.
*C07K 7/00* (2006.01)
*A61K 38/16* (2006.01)
*A61P 31/18* (2006.01)

(52) U.S. Cl. ............................ 530/324; 514/3.7; 514/3.8

(58) Field of Classification Search ........................ None
See application file for complete search history.

(56) References Cited

U.S. PATENT DOCUMENTS

| | | |
|---|---|---|
| 4,016,273 A | 4/1977 | Sieger et al. |
| 4,395,405 A | 7/1983 | Noda et al. |
| 4,530,840 A | 7/1985 | Tice et al. |
| 4,629,783 A | 12/1986 | Cosand |
| 4,767,628 A | 8/1988 | Hutchinson |
| 4,938,763 A | 7/1990 | Dunn et al. |
| 5,234,520 A | 8/1993 | McClintock |
| 5,278,202 A | 1/1994 | Dunn et al. |
| 5,278,553 A | 1/1994 | Cornett et al. |
| 5,411,951 A | 5/1995 | Mitchell |
| 5,462,863 A | 10/1995 | Hsieh et al. |
| 5,464,933 A | 11/1995 | Bolognesi et al. |
| 5,589,167 A | 12/1996 | Cleland et al. |
| 5,656,480 A | 8/1997 | Wild et al. |
| 5,728,553 A | 3/1998 | Goodey et al. |
| 5,747,058 A | 5/1998 | Tipton et al. |
| 5,889,035 A | 3/1999 | Strupczewski et al. |
| 5,965,386 A | 10/1999 | Kerry-Williams et al. |
| 6,004,549 A | 12/1999 | Reichert et al. |
| 6,015,881 A | 1/2000 | Kang et al. |
| 6,133,418 A | 10/2000 | Bolognesi et al. |
| 6,143,314 A | 11/2000 | Chandrashekar et al. |
| 6,191,107 B1 | 2/2001 | Yamagata et al. |
| 6,258,782 B1 | 7/2001 | Barney et al. |
| 6,281,331 B1 | 8/2001 | Kang et al. |
| 6,328,979 B1 | 12/2001 | Yamashita et al. |
| 6,348,568 B1 | 2/2002 | Barney et al. |
| 6,475,491 B1 | 11/2002 | Johnson et al. |
| 6,541,020 B1 | 4/2003 | Ding et al. |
| 6,562,787 B1 | 5/2003 | Barney et al. |
| 6,565,874 B1 | 5/2003 | Dunn et al. |
| 6,573,078 B1 | 6/2003 | Wild et al. |
| 6,630,155 B1 | 10/2003 | Chandrashekar et al. |
| 6,656,906 B1 | 12/2003 | Barney et al. |
| 6,773,714 B2 | 8/2004 | Dunn et al. |
| 6,824,783 B1 | 11/2004 | Bolognesi et al. |
| 6,861,059 B2 | 3/2005 | Johnson et al. |
| 6,962,900 B2 | 11/2005 | Zhou et al. |
| 6,992,065 B2 | 1/2006 | Okumu |
| 7,045,552 B2 | 5/2006 | Heilman et al. |
| 7,053,209 B1 | 5/2006 | Gibson et al. |
| 7,318,931 B2 | 1/2008 | Okumu et al. |
| 7,456,251 B2 | 11/2008 | Dwyer et al. |
| 2004/0076602 A1 | 4/2004 | Harris |
| 2005/0226843 A1 | 10/2005 | Bentley et al. |
| 2006/0247416 A1 | 11/2006 | DelMedico |

FOREIGN PATENT DOCUMENTS

| | | |
|---|---|---|
| WO | WO 97/03692 | 2/1997 |
| WO | WO 99/33491 | 7/1999 |
| WO | WO 00/69902 | 11/2000 |
| WO | WO 2005/067960 | 7/2005 |
| WO | WO 2005/089796 | 9/2005 |

OTHER PUBLICATIONS

U.S. Appl. No. 60/214,468, filed Jun. 26, 2000, Jeng & Patel.
Bartus et al., 1998, "Sustained delivery of proteins for novel therapeutic agents." Science 281:1161-1162.
Coombes et al., 1999, "Biodegradable polymeric microparticles for drug delivery and vaccine formulation: the surface attachment of hydrophilic species using the concept of poly(ethylene glycol) anchoring segments." Biomaterials 18(17):1153-1161.
Johnson et al., 1996, "A month-long effect from a single injection of microencapsulated human growth hormone." Nature Med. 2(7):795-799.
Kilby et al., 1998, "Potent suppression of HIV-1 replication in humans by T-20. A peptide inhibitor of gp41-mediated virus entry." Nature Med. 4(11):1302-1307.
Kulkarni et al., 1966, "Polylactic acid for surgical implants." Arch. Surg. 93:839.
Lalezari et al., 2003, "Enfuvirtide, an HIV-1 fusion inhibitor, for drug-resistant HIV infection in North and South America." N. Engl. J. Med :1-10.

(Continued)

*Primary Examiner* — Zachariah Lucas
*Assistant Examiner* — Nicole Kinsey White
(74) *Attorney, Agent, or Firm* — Jones Day

(57) ABSTRACT

Provided is an HIV fusion inhibitor peptide having an amino acid sequence of any one of SEQ ID NO:9, SEQ ID NO:10, SEQ ID NO:11, SEQ ID NO:12, SEQ ID NO:13, SEQ ID NO:14, or SEQ ID NO:15; and provided is a pharmaceutical composition comprising a HIV fusion inhibitor peptide and one or more of a pharmaceutically acceptable carrier and macromolecular carrier, and uses and methods of treatment provided by these compositions.

64 Claims, 4 Drawing Sheets

OTHER PUBLICATIONS

Lawless et al., 1996, "HIV-1 membrane fusion mechanism: structural studies of the interactions between biologically-active peptides from gp41." Biochem 35:13697-13708.

Melby et al., 2006, "Characterization of envelope glycoprotein gp41 genotype and phenotypic susceptibility to enfuvirtide at baseline and on treatment in the phase III clinical trials TORO-1 and TORO-2." AIDS Res & Human Retro. 22(5):375-385.

Middaugh et al., 1979, "Determination of the apparent thermodynamic activities of saturated protein solutions." J. Biol. Chem. 254(3):367-370.

Middaugh et al., 1992, "Protein Solubility." Ch. 4 in "Stability of Protein Pharmaceuticals." Ed.

Otaka et al., 2002, "Effect of zinc binding and precipitation on structures of recombinant human growth hormone and nerve growth factor" Angewandte Chemie Interantional Ed. 41:2937-2940.

Rusconi et al., 2004, "Entry and fusion inhibitors in HIV." Expert Opin. Ther. Patients 14(5):733-748.

Sia et al., 2002, "Short constrained peptides that inhibit HIV-1 entry" Proc. Natl. Acad. Sci. 99:14664-14669.

Sista et al., 2004, "Characterization of determinants of genotypic and phenotypic resistance to enfuvirtide in baseline and on-treatment HIV-1 isolates." AIDS 18:1787-1794.

Smith & Tipton, 1996, "A novel parenteral delivery system" Pharma Res. 13(3):300.

Swiderski et al., 1966, "Application of 14C isotope in studies on the lability of sugar substituents" Nukleonika Supl. 10:347-352, Summary Only.

Wild et al., 1994, "Peptides corresponding to a predictive alpha-helical domain of human immunodeficiency virus type 1 gp41 are potent inhibitors of virus infection." Proc. Natl. Acad. Sci 91:9770-9774.

Yang et al., 2000, "Effect of zinc binding and precipitation on structures of recombinant human growth hormone and nerve growth factor." J. Pharma Sci 89(11):1480-1485.

Examination Report dated May 12, 2009 in relation to EP Application EP07749903.6 based on PCT/US2007/002990.

Response pursuant to Article 94(3) EPC dated Nov. 23, 2009 in relation to EP Application EP07749903.6 based on PCT/US2007/002990.

FIG. 2

```
    MTWMEWDREINNYTSLIHSLIEESQNQQEKNEQELL
    ---------+---------+---------+------
            10        20        30
    ---------+---------+---------+------  Isolate
624 MTWMEWDREINNYTSLIHSLIEESQNQQEKNEQELL  NL4-3
631 MTWMEWDREINNYTSLIHSLIEESQNQQEKNEQELL  LAV1a
626 TTWMEWDREINNYTSLIHSLIEESQNQQEKNEQELL  IIIB
626 TTWMEWDREINNYTSLIHSLIEESQNQQEKNEQELL  HXB2
619 MTWMQWEKEINNYTGLIYNLIEESQNQQEKNEQELL  DH12
    MTWMEWDREINNYTSLIHSLIEESQNQQEKNEQELL  BRU
    TTWMEWDREINNYTSLIHSLIEESQNQQEKNEQELL  HXB2
    MTWMEWDREINNYTSLIHSLIEESQNQQEKNEQELL  pNL4-3
625 MTWLQWDKEISNYTNIIYDLIEEAQNQQEKNEQDLL  Ug273-A
623 MTWMEWEREIDNYTNTIYTLLEESQLQQEKNEQELL  Us2-B
619 MTWMQWDREISNYTGTIYRLLEDSQNQQEKNEKDLL  Ug268-C
    MTWMEWEREIDNYTGLIYSLIEESQTQQEKNEQELL  Se365-D
620 MTWIEWEREISNYTNQIYEILTESQNQQDRNEKDLL  CM240-E
612 MTWMEWEKEISNYSYEIYRLIEQSQNQQEKNEQELL  Bz126-F
613 MTWIQWDREISNYTQQIYSLIEESQNQQEKNEQDLL  HH8793-G
```

SEQUENCE LISTING

```
<160> NUMBER OF SEQ ID NOS: 56

<210> SEQ ID NO 1
<211> LENGTH: 64
<212> TYPE: PRT
<213> ORGANISM: Artificial Sequence
<220> FEATURE:
<223> OTHER INFORMATION: synthesized peptide

<400> SEQUENCE: 1

Trp Asn Ala Ser Trp Ser Asn Lys Ser Leu Glu Gln Ile Trp Asn Asn
1               5                   10                  15

Met Thr Trp Met Glu Trp Asp Arg Glu Ile Asn Asn Tyr Thr Ser Leu
            20                  25                  30

Ile His Ser Leu Ile Glu Glu Ser Gln Asn Gln Gln Glu Lys Asn Glu
        35                  40                  45

Gln Glu Leu Leu Glu Leu Asp Lys Trp Ala Ser Leu Trp Asn Trp Phe
    50                  55                  60

<210> SEQ ID NO 2
<211> LENGTH: 36
<212> TYPE: PRT
<213> ORGANISM: Artificial Sequence
<220> FEATURE:
<223> OTHER INFORMATION: synthesized peptide

<400> SEQUENCE: 2

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
```

```
                    20                  25                  30

Trp Asn Trp Phe
        35

<210> SEQ ID NO 3
<211> LENGTH: 36
<212> TYPE: PRT
<213> ORGANISM: Artificial Sequence
<220> FEATURE:
<223> OTHER INFORMATION: synthesized peptide

<400> SEQUENCE: 3

Met Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu
        35

<210> SEQ ID NO 4
<211> LENGTH: 36
<212> TYPE: PRT
<213> ORGANISM: Artificial Sequence
<220> FEATURE:
<223> OTHER INFORMATION: synthesized peptide

<400> SEQUENCE: 4

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Glu Leu
        35

<210> SEQ ID NO 5
<211> LENGTH: 38
<212> TYPE: PRT
<213> ORGANISM: Artificial Sequence
<220> FEATURE:
<223> OTHER INFORMATION: synthesized peptide

<400> SEQUENCE: 5

Thr Thr Trp Glu Ala Trp Asp Arg Ala Ile Ala Glu Tyr Ala Ala Arg
1               5                   10                  15

Ile Glu Ala Leu Ile Arg Ala Gln Glu Gln Gln Glu Lys Asn Glu
            20                  25                  30

Ala Ala Leu Arg Glu Leu
        35

<210> SEQ ID NO 6
<211> LENGTH: 38
<212> TYPE: PRT
<213> ORGANISM: Artificial Sequence
<220> FEATURE:
<223> OTHER INFORMATION: synthesized peptide

<400> SEQUENCE: 6

Thr Thr Trp Glu Ala Trp Asp Arg Ala Ile Ala Glu Tyr Ala Ala Arg
1               5                   10                  15

Ile Glu Ala Leu Ile Arg Ala Leu Gln Glu Gln Gln Glu Lys Asn Glu
            20                  25                  30

Ala Ala Leu Arg Glu Leu
        35
```

<210> SEQ ID NO 7
<211> LENGTH: 38
<212> TYPE: PRT
<213> ORGANISM: Artificial Sequence
<220> FEATURE:
<223> OTHER INFORMATION: synthesized peptide

<400> SEQUENCE: 7

Thr Thr Trp Glu Ala Trp Asp Arg Ala Ile Ala Glu Tyr Ala Ala Arg
1               5                   10                  15

Ile Glu Ala Leu Ile Arg Ala Ala Gln Glu Gln Gln Glu Lys Leu Glu
            20                  25                  30

Ala Ala Leu Arg Glu Leu
        35

<210> SEQ ID NO 8
<211> LENGTH: 38
<212> TYPE: PRT
<213> ORGANISM: Artificial Sequence
<220> FEATURE:
<223> OTHER INFORMATION: synthesized peptide

<400> SEQUENCE: 8

Thr Thr Trp Glu Ala Trp Asp Arg Ala Ile Ala Glu Tyr Ala Ala Arg
1               5                   10                  15

Ile Glu Ala Leu Leu Arg Ala Ala Gln Glu Gln Gln Glu Lys Asn Glu
            20                  25                  30

Ala Ala Leu Arg Glu Leu
        35

<210> SEQ ID NO 9
<211> LENGTH: 38
<212> TYPE: PRT
<213> ORGANISM: Artificial Sequence
<220> FEATURE:
<223> OTHER INFORMATION: synthesized peptide

<400> SEQUENCE: 9

Thr Thr Trp Glu Ala Trp Asp Arg Ala Ile Ala Glu Tyr Ala Ala Arg
1               5                   10                  15

Ile Glu Ala Leu Leu Arg Ala Leu Gln Glu Gln Gln Glu Lys Asn Glu
            20                  25                  30

Ala Ala Leu Arg Glu Leu
        35

<210> SEQ ID NO 10
<211> LENGTH: 38
<212> TYPE: PRT
<213> ORGANISM: Artificial Sequence
<220> FEATURE:
<223> OTHER INFORMATION: synthesized peptide

<400> SEQUENCE: 10

Thr Thr Trp Glu Ala Trp Asp Arg Ala Ile Ala Glu Tyr Ala Ala Arg
1               5                   10                  15

Ile Glu Ala Leu Leu Arg Ala Ala Gln Glu Gln Gln Glu Lys Leu Glu
            20                  25                  30

Ala Ala Leu Arg Glu Leu
        35

<210> SEQ ID NO 11
<211> LENGTH: 38

```
<212> TYPE: PRT
<213> ORGANISM: Artificial Sequence
<220> FEATURE:
<223> OTHER INFORMATION: synthesized peptide

<400> SEQUENCE: 11

Thr Thr Trp Glu Ala Trp Asp Arg Ala Ile Ala Glu Tyr Ala Ala Arg
1               5                   10                  15

Ile Glu Ala Leu Ile Arg Ala Leu Gln Glu Gln Gln Glu Lys Leu Glu
            20                  25                  30

Ala Ala Leu Arg Glu Leu
        35

<210> SEQ ID NO 12
<211> LENGTH: 38
<212> TYPE: PRT
<213> ORGANISM: Artificial Sequence
<220> FEATURE:
<223> OTHER INFORMATION: synthesized peptide

<400> SEQUENCE: 12

Thr Thr Trp Glu Ala Trp Asp Arg Ala Ile Ala Glu Tyr Ala Ala Arg
1               5                   10                  15

Ile Glu Ala Leu Ile Arg Ala Ile Gln Glu Gln Gln Glu Lys Leu Glu
            20                  25                  30

Ala Ala Leu Arg Glu Leu
        35

<210> SEQ ID NO 13
<211> LENGTH: 38
<212> TYPE: PRT
<213> ORGANISM: Artificial Sequence
<220> FEATURE:
<223> OTHER INFORMATION: synthesized peptide

<400> SEQUENCE: 13

Thr Thr Trp Glu Ala Trp Asp Arg Ala Ile Ala Glu Tyr Ala Ala Arg
1               5                   10                  15

Ile Glu Ala Leu Ile Arg Ala Leu Gln Glu Gln Gln Glu Lys Ile Glu
            20                  25                  30

Ala Ala Leu Arg Glu Leu
        35

<210> SEQ ID NO 14
<211> LENGTH: 38
<212> TYPE: PRT
<213> ORGANISM: Artificial Sequence
<220> FEATURE:
<223> OTHER INFORMATION: synthesized peptide

<400> SEQUENCE: 14

Thr Thr Trp Glu Ala Trp Asp Arg Ala Ile Ala Glu Tyr Ala Ala Arg
1               5                   10                  15

Ile Glu Ala Leu Leu Arg Ala Ile Gln Glu Gln Gln Glu Lys Asn Glu
            20                  25                  30

Ala Ala Leu Arg Glu Leu
        35

<210> SEQ ID NO 15
<211> LENGTH: 38
<212> TYPE: PRT
<213> ORGANISM: Artificial Sequence
<220> FEATURE:
<223> OTHER INFORMATION: synthesized peptide
```

-continued

```
<400> SEQUENCE: 15

Thr Thr Trp Glu Ala Trp Asp Arg Ala Ile Ala Glu Tyr Ala Ala Arg
1               5                   10                  15

Ile Glu Ala Leu Leu Arg Ala Ala Gln Glu Gln Gln Glu Lys Ile Glu
            20                  25                  30

Ala Ala Leu Arg Glu Leu
        35

<210> SEQ ID NO 16
<211> LENGTH: 38
<212> TYPE: PRT
<213> ORGANISM: Artificial Sequence
<220> FEATURE:
<223> OTHER INFORMATION: synthesized peptide
<220> FEATURE:
<221> NAME/KEY: misc_feature
<222> LOCATION: (1)..(3)
<223> OTHER INFORMATION: Xaa = any amino acid
<220> FEATURE:
<221> NAME/KEY: misc_feature
<222> LOCATION: (6)..(6)
<223> OTHER INFORMATION: Xaa = any amino acid
<220> FEATURE:
<221> NAME/KEY: misc_feature
<222> LOCATION: (10)..(10)
<223> OTHER INFORMATION: Xaa = leucine or isoleucine
<220> FEATURE:
<221> NAME/KEY: misc_feature
<222> LOCATION: (13)..(13)
<223> OTHER INFORMATION: Xaa = any amino acid
<220> FEATURE:
<221> NAME/KEY: misc_feature
<222> LOCATION: (17)..(17)
<223> OTHER INFORMATION: Xaa = leucine or isoleucine
<220> FEATURE:
<221> NAME/KEY: misc_feature
<222> LOCATION: (20)..(21)
<223> OTHER INFORMATION: Xaa = leucine or isoleucine
<220> FEATURE:
<221> NAME/KEY: misc_feature
<222> LOCATION: (24)..(24)
<223> OTHER INFORMATION: Xaa = any amino acid, preferably leucine or
      isoleucine
<220> FEATURE:
<221> NAME/KEY: misc_feature
<222> LOCATION: (25)..(25)
<223> OTHER INFORMATION: Xaa = any amino acid
<220> FEATURE:
<221> NAME/KEY: misc_feature
<222> LOCATION: (27)..(28)
<223> OTHER INFORMATION: Xaa = any amino acid
<220> FEATURE:
<221> NAME/KEY: misc_feature
<222> LOCATION: (31)..(31)
<223> OTHER INFORMATION: Xaa = any amino acid, preferably leucine or
      isoleucine
<220> FEATURE:
<221> NAME/KEY: misc_feature
<222> LOCATION: (35)..(35)
<223> OTHER INFORMATION: Xaa = leucine or isoleucine
<220> FEATURE:
<221> NAME/KEY: misc_feature
<222> LOCATION: (38)..(38)
<223> OTHER INFORMATION: Xaa = leucine or isoleucine

<400> SEQUENCE: 16

Xaa Xaa Xaa Glu Ala Xaa Asp Arg Ala Xaa Ala Glu Xaa Ala Ala Arg
1               5                   10                  15

Xaa Glu Ala Xaa Xaa Arg Ala Xaa Xaa Glu Xaa Xaa Glu Lys Xaa Glu
            20                  25                  30

Ala Ala Xaa Arg Glu Xaa
        35
```

```
<210> SEQ ID NO 17
<211> LENGTH: 12
<212> TYPE: PRT
<213> ORGANISM: Artificial Sequence
<220> FEATURE:
<223> OTHER INFORMATION: synthesized peptide

<400> SEQUENCE: 17

Thr Thr Trp Glu Ala Trp Asp Arg Ala Ile Ala Glu
1               5                   10

<210> SEQ ID NO 18
<211> LENGTH: 14
<212> TYPE: PRT
<213> ORGANISM: Artificial Sequence
<220> FEATURE:
<223> OTHER INFORMATION: synthesized peptide

<400> SEQUENCE: 18

Tyr Ala Ala Arg Ile Glu Ala Leu Leu Arg Ala Leu Gln Glu
1               5                   10

<210> SEQ ID NO 19
<211> LENGTH: 11
<212> TYPE: PRT
<213> ORGANISM: Artificial Sequence
<220> FEATURE:
<223> OTHER INFORMATION: synthesized peptide

<400> SEQUENCE: 19

Gln Gln Glu Lys Asn Glu Ala Ala Leu Arg Glu
1               5                   10

<210> SEQ ID NO 20
<211> LENGTH: 12
<212> TYPE: PRT
<213> ORGANISM: Artificial Sequence
<220> FEATURE:
<223> OTHER INFORMATION: synthesized peptide

<400> SEQUENCE: 20

Gln Gln Glu Lys Asn Glu Ala Ala Leu Arg Glu Leu
1               5                   10

<210> SEQ ID NO 21
<211> LENGTH: 11
<212> TYPE: PRT
<213> ORGANISM: Artificial Sequence
<220> FEATURE:
<223> OTHER INFORMATION: synthesized peptide

<400> SEQUENCE: 21

Thr Thr Trp Glu Ala Trp Asp Arg Ala Ile Ala
1               5                   10

<210> SEQ ID NO 22
<211> LENGTH: 15
<212> TYPE: PRT
<213> ORGANISM: Artificial Sequence
<220> FEATURE:
<223> OTHER INFORMATION: synthesized peptide

<400> SEQUENCE: 22

Glu Tyr Ala Ala Arg Ile Glu Ala Leu Leu Arg Ala Leu Gln Glu
1               5                   10                  15
```

```
<210> SEQ ID NO 23
<211> LENGTH: 10
<212> TYPE: PRT
<213> ORGANISM: Artificial Sequence
<220> FEATURE:
<223> OTHER INFORMATION: synthesized peptide

<400> SEQUENCE: 23

Thr Thr Trp Glu Ala Trp Asp Arg Ala Ile
1               5                   10

<210> SEQ ID NO 24
<211> LENGTH: 16
<212> TYPE: PRT
<213> ORGANISM: Artificial Sequence
<220> FEATURE:
<223> OTHER INFORMATION: synthesized peptide

<400> SEQUENCE: 24

Ala Glu Tyr Ala Ala Arg Ile Glu Ala Leu Leu Arg Ala Leu Gln Glu
1               5                   10                  15

<210> SEQ ID NO 25
<211> LENGTH: 9
<212> TYPE: PRT
<213> ORGANISM: Artificial Sequence
<220> FEATURE:
<223> OTHER INFORMATION: synthesized peptide

<400> SEQUENCE: 25

Thr Thr Trp Glu Ala Trp Asp Arg Ala
1               5

<210> SEQ ID NO 26
<211> LENGTH: 17
<212> TYPE: PRT
<213> ORGANISM: Artificial Sequence
<220> FEATURE:
<223> OTHER INFORMATION: synthesized peptide

<400> SEQUENCE: 26

Ile Ala Glu Tyr Ala Ala Arg Ile Glu Ala Leu Leu Arg Ala Leu Gln
1               5                   10                  15

Glu

<210> SEQ ID NO 27
<211> LENGTH: 8
<212> TYPE: PRT
<213> ORGANISM: Artificial Sequence
<220> FEATURE:
<223> OTHER INFORMATION: synthesized peptide

<400> SEQUENCE: 27

Thr Thr Trp Glu Ala Trp Asp Arg
1               5

<210> SEQ ID NO 28
<211> LENGTH: 18
<212> TYPE: PRT
<213> ORGANISM: Artificial Sequence
<220> FEATURE:
<223> OTHER INFORMATION: synthesized peptide

<400> SEQUENCE: 28

Ala Ile Ala Glu Tyr Ala Ala Arg Ile Glu Ala Leu Leu Arg Ala Leu
1               5                   10                  15

Gln Glu
```

```
<210> SEQ ID NO 29
<211> LENGTH: 20
<212> TYPE: PRT
<213> ORGANISM: Artificial Sequence
<220> FEATURE:
<223> OTHER INFORMATION: synthesized peptide

<400> SEQUENCE: 29

Thr Thr Trp Glu Ala Trp Asp Arg Ala Ile Ala Glu Tyr Ala Ala Arg
1               5                   10                  15

Ile Glu Ala Leu
            20

<210> SEQ ID NO 30
<211> LENGTH: 17
<212> TYPE: PRT
<213> ORGANISM: Artificial Sequence
<220> FEATURE:
<223> OTHER INFORMATION: synthesized peptide

<400> SEQUENCE: 30

Leu Arg Ala Leu Gln Glu Gln Gln Glu Lys Asn Glu Ala Ala Leu Arg
1               5                   10                  15

Glu

<210> SEQ ID NO 31
<211> LENGTH: 18
<212> TYPE: PRT
<213> ORGANISM: Artificial Sequence
<220> FEATURE:
<223> OTHER INFORMATION: synthesized peptide

<400> SEQUENCE: 31

Leu Arg Ala Leu Gln Glu Gln Gln Glu Lys Asn Glu Ala Ala Leu Arg
1               5                   10                  15

Glu Leu

<210> SEQ ID NO 32
<211> LENGTH: 18
<212> TYPE: PRT
<213> ORGANISM: Artificial Sequence
<220> FEATURE:
<223> OTHER INFORMATION: synthesized peptide

<400> SEQUENCE: 32

Thr Thr Trp Glu Ala Trp Asp Arg Ala Ile Ala Glu Tyr Ala Ala Arg
1               5                   10                  15

Ile Glu

<210> SEQ ID NO 33
<211> LENGTH: 19
<212> TYPE: PRT
<213> ORGANISM: Artificial Sequence
<220> FEATURE:
<223> OTHER INFORMATION: synthesized peptide

<400> SEQUENCE: 33

Ala Leu Leu Arg Ala Leu Gln Glu Gln Gln Glu Lys Asn Glu Ala Ala
1               5                   10                  15

Leu Arg Glu

<210> SEQ ID NO 34
<211> LENGTH: 20
```

```
<212> TYPE: PRT
<213> ORGANISM: Artificial Sequence
<220> FEATURE:
<223> OTHER INFORMATION: synthesized peptide

<400> SEQUENCE: 34

Ala Leu Leu Arg Ala Leu Gln Glu Gln Gln Glu Lys Asn Glu Ala Ala
1               5                   10                  15

Leu Arg Glu Leu
            20

<210> SEQ ID NO 35
<211> LENGTH: 26
<212> TYPE: PRT
<213> ORGANISM: Artificial Sequence
<220> FEATURE:
<223> OTHER INFORMATION: synthesized peptide

<400> SEQUENCE: 35

Tyr Ala Ala Arg Ile Glu Ala Leu Leu Arg Ala Leu Gln Glu Gln Gln
1               5                   10                  15

Glu Lys Asn Glu Ala Ala Leu Arg Glu Leu
            20                  25

<210> SEQ ID NO 36
<211> LENGTH: 27
<212> TYPE: PRT
<213> ORGANISM: Artificial Sequence
<220> FEATURE:
<223> OTHER INFORMATION: synthesized peptide

<400> SEQUENCE: 36

Glu Tyr Ala Ala Arg Ile Glu Ala Leu Leu Arg Ala Leu Gln Glu Gln
1               5                   10                  15

Gln Glu Lys Asn Glu Ala Ala Leu Arg Glu Leu
            20                  25

<210> SEQ ID NO 37
<211> LENGTH: 28
<212> TYPE: PRT
<213> ORGANISM: Artificial Sequence
<220> FEATURE:
<223> OTHER INFORMATION: synthesized peptide

<400> SEQUENCE: 37

Ala Glu Tyr Ala Ala Arg Ile Glu Ala Leu Leu Arg Ala Leu Gln Glu
1               5                   10                  15

Gln Gln Glu Lys Asn Glu Ala Ala Leu Arg Glu Leu
            20                  25

<210> SEQ ID NO 38
<211> LENGTH: 29
<212> TYPE: PRT
<213> ORGANISM: Artificial Sequence
<220> FEATURE:
<223> OTHER INFORMATION: synthesized peptide

<400> SEQUENCE: 38

Ile Ala Glu Tyr Ala Ala Arg Ile Glu Ala Leu Leu Arg Ala Leu Gln
1               5                   10                  15

Glu Gln Gln Glu Lys Asn Glu Ala Ala Leu Arg Glu Leu
            20                  25

<210> SEQ ID NO 39
<211> LENGTH: 30
```

```
<212> TYPE: PRT
<213> ORGANISM: Artificial Sequence
<220> FEATURE:
<223> OTHER INFORMATION: synthesized peptide

<400> SEQUENCE: 39

Ala Ile Ala Glu Tyr Ala Ala Arg Ile Glu Ala Leu Leu Arg Ala Leu
1               5                   10                  15

Gln Glu Gln Gln Glu Lys Asn Glu Ala Ala Leu Arg Glu Leu
            20                  25                  30

<210> SEQ ID NO 40
<211> LENGTH: 26
<212> TYPE: PRT
<213> ORGANISM: Artificial Sequence
<220> FEATURE:
<223> OTHER INFORMATION: synthesized peptide

<400> SEQUENCE: 40

Thr Thr Trp Glu Ala Trp Asp Arg Ala Ile Ala Glu Tyr Ala Ala Arg
1               5                   10                  15

Ile Glu Ala Leu Leu Arg Ala Leu Gln Glu
            20                  25

<210> SEQ ID NO 41
<211> LENGTH: 14
<212> TYPE: PRT
<213> ORGANISM: Artificial Sequence
<220> FEATURE:
<223> OTHER INFORMATION: synthesized peptide

<400> SEQUENCE: 41

Tyr Ala Ala Arg Ile Glu Ala Leu Leu Arg Ala Ala Gln Glu
1               5                   10

<210> SEQ ID NO 42
<211> LENGTH: 11
<212> TYPE: PRT
<213> ORGANISM: Artificial Sequence
<220> FEATURE:
<223> OTHER INFORMATION: synthesized peptide

<400> SEQUENCE: 42

Gln Gln Glu Lys Leu Glu Ala Ala Leu Arg Glu
1               5                   10

<210> SEQ ID NO 43
<211> LENGTH: 12
<212> TYPE: PRT
<213> ORGANISM: Artificial Sequence
<220> FEATURE:
<223> OTHER INFORMATION: synthesized peptide

<400> SEQUENCE: 43

Gln Gln Glu Lys Leu Glu Ala Ala Leu Arg Glu Leu
1               5                   10

<210> SEQ ID NO 44
<211> LENGTH: 15
<212> TYPE: PRT
<213> ORGANISM: Artificial Sequence
<220> FEATURE:
<223> OTHER INFORMATION: synthesized peptide

<400> SEQUENCE: 44

Glu Tyr Ala Ala Arg Ile Glu Ala Leu Leu Arg Ala Ala Gln Glu
1               5                   10                  15
```

-continued

```
<210> SEQ ID NO 45
<211> LENGTH: 16
<212> TYPE: PRT
<213> ORGANISM: Artificial Sequence
<220> FEATURE:
<223> OTHER INFORMATION: synthesized peptide

<400> SEQUENCE: 45

Ala Glu Tyr Ala Ala Arg Ile Glu Ala Leu Leu Arg Ala Ala Gln Glu
1               5                   10                  15

<210> SEQ ID NO 46
<211> LENGTH: 17
<212> TYPE: PRT
<213> ORGANISM: Artificial Sequence
<220> FEATURE:
<223> OTHER INFORMATION: synthesized peptide

<400> SEQUENCE: 46

Ile Ala Glu Tyr Ala Ala Arg Ile Glu Ala Leu Leu Arg Ala Ala Gln
1               5                   10                  15

Glu

<210> SEQ ID NO 47
<211> LENGTH: 18
<212> TYPE: PRT
<213> ORGANISM: Artificial Sequence
<220> FEATURE:
<223> OTHER INFORMATION: synthesized peptide

<400> SEQUENCE: 47

Ala Ile Ala Glu Tyr Ala Ala Arg Ile Glu Ala Leu Leu Arg Ala Ala
1               5                   10                  15

Gln Glu

<210> SEQ ID NO 48
<211> LENGTH: 17
<212> TYPE: PRT
<213> ORGANISM: Artificial Sequence
<220> FEATURE:
<223> OTHER INFORMATION: synthesized peptide

<400> SEQUENCE: 48

Leu Arg Ala Ala Gln Glu Gln Gln Glu Lys Leu Glu Ala Ala Leu Arg
1               5                   10                  15

Glu

<210> SEQ ID NO 49
<211> LENGTH: 19
<212> TYPE: PRT
<213> ORGANISM: Artificial Sequence
<220> FEATURE:
<223> OTHER INFORMATION: synthesized peptide

<400> SEQUENCE: 49

Leu Arg Ala Ala Leu Gln Glu Gln Gln Glu Lys Leu Glu Ala Ala Leu
1               5                   10                  15

Arg Glu Leu

<210> SEQ ID NO 50
<211> LENGTH: 19
<212> TYPE: PRT
<213> ORGANISM: Artificial Sequence
<220> FEATURE:
```

-continued

<223> OTHER INFORMATION: synthesized peptide

<400> SEQUENCE: 50

Ala Leu Leu Arg Ala Ala Gln Glu Gln Gln Glu Lys Leu Glu Ala Ala
1               5                   10                  15

Leu Arg Glu

<210> SEQ ID NO 51
<211> LENGTH: 20
<212> TYPE: PRT
<213> ORGANISM: Artificial Sequence
<220> FEATURE:
<223> OTHER INFORMATION: synthesized peptide

<400> SEQUENCE: 51

Ala Leu Leu Arg Ala Ala Gln Glu Gln Gln Glu Lys Leu Glu Ala Ala
1               5                   10                  15

Leu Arg Glu Leu
            20

<210> SEQ ID NO 52
<211> LENGTH: 26
<212> TYPE: PRT
<213> ORGANISM: Artificial Sequence
<220> FEATURE:
<223> OTHER INFORMATION: synthesized peptide

<400> SEQUENCE: 52

Tyr Ala Ala Arg Ile Glu Ala Leu Leu Arg Ala Ala Gln Glu Gln Gln
1               5                   10                  15

Glu Lys Leu Glu Ala Ala Leu Arg Glu Leu
            20                  25

<210> SEQ ID NO 53
<211> LENGTH: 27
<212> TYPE: PRT
<213> ORGANISM: Artificial Sequence
<220> FEATURE:
<223> OTHER INFORMATION: synthesized peptide

<400> SEQUENCE: 53

Glu Tyr Ala Ala Arg Ile Glu Ala Leu Leu Arg Ala Ala Gln Glu Gln
1               5                   10                  15

Gln Glu Lys Leu Glu Ala Ala Leu Arg Glu Leu
            20                  25

<210> SEQ ID NO 54
<211> LENGTH: 28
<212> TYPE: PRT
<213> ORGANISM: Artificial Sequence
<220> FEATURE:
<223> OTHER INFORMATION: synthesized peptide

<400> SEQUENCE: 54

Ala Glu Tyr Ala Ala Arg Ile Glu Ala Leu Leu Arg Ala Ala Gln Glu
1               5                   10                  15

Gln Gln Glu Lys Leu Glu Ala Ala Leu Arg Glu Leu
            20                  25

<210> SEQ ID NO 55
<211> LENGTH: 29
<212> TYPE: PRT
<213> ORGANISM: Artificial Sequence
<220> FEATURE:
<223> OTHER INFORMATION: synthesized peptide -continued

```
<400> SEQUENCE: 55

Ile Ala Glu Tyr Ala Ala Arg Ile Glu Ala Leu Leu Arg Ala Ala Gln
1               5                   10                  15

Glu Gln Gln Glu Lys Leu Glu Ala Ala Leu Arg Glu Leu
            20                  25

<210> SEQ ID NO 56
<211> LENGTH: 30
<212> TYPE: PRT
<213> ORGANISM: Artificial Sequence
<220> FEATURE:
<223> OTHER INFORMATION: synthesized peptide

<400> SEQUENCE: 56

Ala Ile Ala Glu Tyr Ala Ala Arg Ile Glu Ala Leu Leu Arg Ala Ala
1               5                   10                  15

Gln Glu Gln Gln Glu Lys Leu Glu Ala Ala Leu Arg Glu Leu
            20                  25                  30
```

US 8,034,899 B2

HIV FUSION INHIBITOR PEPTIDES WITH IMPROVED BIOLOGICAL PROPERTIES

1. CROSS REFERENCE TO RELATED APPLICATIONS

This application is a continuation application of U.S. patent application Ser. No. 11/701,910 filed Feb. 2, 2007, now U.S. Pat. No. 7,456,251, which claims priority to U.S. Provisional Application No. 60/764,674 filed Feb. 2, 2006, the entire contents of which are incorporated by reference.

2. FIELD OF INVENTION

The present invention relates to a synthetic peptide derived from the amino acid sequence of Human Immunodeficiency Virus (HIV) gp41. More specifically, the present invention relates to an HIV fusion inhibitor peptide having certain amino acid differences, as compared to the natural amino acid sequence of HIV gp41, which confer beneficial biological properties to the HIV fusion inhibitor peptide.

3. BACKGROUND OF THE INVENTION

It is now well known that cells can be infected by HIV through a process by which fusion occurs between the cellular membrane and the viral membrane. The generally accepted model of this process is that the viral envelope glycoprotein complex (gp120/gp41) interacts with cell surface receptors on the membranes of the target cells. Following binding of gp120 to cellular receptors (e.g., CD4 in combination with a chemokine co-receptor such as CCR-5 or CXCR-4), a conformational change is induced in the gp120/gp41 complex that allows gp41 to insert into the membrane of the target cell and mediate membrane fusion.

The amino acid sequence of gp41, and its variation among different strains of HIV, is well known. FIG. 1 is a schematic representation of the generally accepted functional domains of gp41 (note the amino acid sequence numbers may vary slightly depending on the HIV strain). The fusogenic domain is believed to be involved in insertion into and disruption of the target cell membrane. The transmembrane domain, containing the transmembrane anchor sequence, is located at the C-terminal end of the protein. Between the fusogenic domain and transmembrane anchor are two distinct regions, known as heptad repeat (HR) regions, each region having a plurality of heptads. The amino acid sequence comprising the HR1 region and the amino acid sequence comprising the HR2 region are each highly conserved regions in the HIV-1 envelope protein. The HR2 region has been generally described as comprising amino acid residues of SEQ ID NO:1, or polymorphisms thereof (see, e.g., FIG. 2). As further shown in FIG. 1, the HR regions have a plurality of 7 amino acid residue stretches or "heptads" (the 7 amino acids in each heptad designated "a" through "g"), with a predominance of hydrophobic residues at the first ("a") and fourth ("d") positions, and charged residues frequently at the fifth ("e") and seventh ("g") positions. Also present in the amino acid sequence of HIV gp41 are leucine zipper-like motifs comprising an 8 amino acid sequence initiating with, and ending with, either an isoleucine or leucine. As illustrated in FIG. 1, the HR2 region has just one leucine zipper like-motif, whereas the HR1 region has five leucine zipper-like motifs. The heptads and a leucine zipper-like motif are amino acid sequence features thought to contribute to formation of the coiled coil structure found for gp41.

It was discovered that peptides derived from the natural sequence of either the HR1 region ("HR1 peptides") or HR2 region ("HR2 peptides") of HIV gp41 inhibit transmission of HIV to host cells both in in vitro assays and in in vivo clinical studies. For example, HR2 peptides, as exemplified by DP178 (also known as T20, enfuvirtide, and Fuzeon®; SEQ ID NO:2), T651 (SEQ ID NO:3), T649 (SEQ ID NO:4), blocked infection of target cells with potencies of 0.5 ng/ml (EC50 against HIV-1$_{LAI}$), 5 ng/ml (IC50; HIV-1 IIIB), and 2 ng/ml (IC50; HIV-1 IIIB), respectively. Efforts have been made to improve the biological activity of HIV gp41-derived peptides, such as by trying to stabilize the helical structure of the peptide. For example, synthetic peptides having helix stabilization are disclosed by the present inventors in PCT publication WO 2005/067960, and are exemplified as SEQ ID NOs:5-7 herein. Synthetic peptides which can inhibit HIV fusion (a process by which HIV gp41 mediates fusion between the viral membrane and the membrane of the cell during the infection process by HIV of a target cell) are a class of peptides often referred to as HIV fusion inhibitor peptides.

Another drawback associated with synthetic peptides relates to the solubility and stability in aqueous-based pharmaceutically acceptable carriers, such as relating to the process of making an injectable solution formulation of an HIV fusion inhibitor peptide. For example, it is difficult to achieve an injectable aqueous solution containing a synthetic peptide having an amino acid sequence of SEQ ID NO:2 in a concentration of more than 100 mg/ml without encountering problems of solubility (wherein the formulation resembles a gel, rather than a solution, or peptide precipitates out of solution over a predetermined time period) and stability (peptide being degraded over a predetermined period of time), and without adding additional components to the formulation to promote stability and/or solubility. Also it would be desirable to develop an HIV fusion inhibitor peptide having improved solubility and stability, while also having improved pharmacological properties.

Thus, there is a need for an HIV fusion inhibitor peptide which: (a) when added in an effective amount, can interfere with the viral fusion process mediated by HIV gp41, and more preferably, interfere with the conformational changes of gp41 necessary to effect fusion, thereby inhibiting the fusion of HIV gp41 to a target cell membrane; (b) demonstrates improved solubility and stability in an aqueous solution; and (c) demonstrates improved pharmacological properties. The present invention addresses these needs.

4. SUMMARY OF THE INVENTION

The present invention relates to isolated peptides that are HIV fusion inhibitor peptides.

In one aspect, the present invention relates to HIV fusion inhibitor peptides derived from a base amino acid sequence ("base sequence") having an amino acid sequence of SEQ ID NO:5, but wherein each HIV fusion inhibitor peptide differs from the base sequence by having more than one leucine zipper-like motif in its amino acid sequence, and having at least one additional leucine present in its amino acid sequence other than that necessary to form a leucine zipper-like motif (i.e., an amino acid in the sequence other than at amino acid position 1 or 8 of a leucine zipper-like motif, as exemplified by substituting isoleucine by leucine at amino acid position 21 of SEQ ID NO:5).

The present invention also relates to HIV fusion inhibitor peptides derived from a base amino acid sequence ("base sequence") having an amino acid sequence of SEQ ID NO:5, but wherein each HIV fusion inhibitor peptide differs from the base sequence by having more than two leucine zipper-like motif in its amino acid sequence.

The present invention also relates to a series of HIV fusion inhibitor peptides, wherein each HIV fusion inhibitor peptide: (a) contains amino acid sequence derived from the HR2 region of HIV gp41; (b) has an amino acid sequence having not less than 2 and not more than 5 leucine zipper-like motifs; (c) having at least one additional leucine (e.g., compared to a base sequence of any one or more of SEQ ID NOs:5-7) in its amino acid sequence other than at amino acid position 1 or 8 of a leucine zipper-like motif, and (d) preferably demonstrates an improvement in one or more biological properties. In certain embodiments, the HIV fusion inhibitor peptide is between 15 and 60 amino acid residues in length. In one embodiment, the HIV fusion inhibitor peptide further comprises a N-terminal group or C-terminal group, or both; those terminal groups may include, but are not limited to: an amino group or an acetyl group at the N-terminus; and a carboxyl group or an amido group at the C-terminus. In one embodiment, the HIV fusion inhibitor peptide may self-associate to form a multimer, e.g., a trimer, or be synthesized in multimeric form, e.g., as a trimer.

In certain embodiments, the HIV fusion inhibitor peptides of the invention are between 15 and 60 amino acids in length, as long as these peptides exhibit at least two leucine zipper-like motifs and exhibit at least one additional isoleucine or leucine not necessary for the formation of a leucine zipper-like motif (e.g., at position 21 of SEQ ID NO:9 or SEQ ID NO:16).

For example, a peptide of a length longer or shorter in amino acid length than SEQ ID NO:16 is considered to be within the scope of the present invention as long as such peptides exhibit at least two leucine zipper-like motifs and exhibit at least one additional isoleucine not necessary for the formation of a leucine zipper-like motif. In instances where the peptide of the invention are longer than the length of SEQ ID NO:5 or SEQ ID NO:16, the additional amino acid residues can, for example, be derived from HIV gp41 amino acid sequences normally adjacent to (either amino and/or carboxy to) the portion of gp41 corresponding to SEQ ID NO:5 by standard alignment techniques.

The present invention also relates to a series of HIV fusion inhibitor peptides, wherein each HIV fusion inhibitor peptide: (a) contains amino acid sequence derived from the HR2 region of HIV gp41; (b) has an amino acid sequence having greater than 2 and not more than 5 leucine zipper-like motifs; and (c) having at least one additional leucine (e.g., compared to a base sequence of any one or more of SEQ ID NOs:5-7) in its amino acid sequence other than at amino acid position 1 or 8 of a leucine zipper-like motif, and (d) preferably demonstrates an improvement in one or more biological properties. In certain embodiments, the HIV fusion inhibitor peptide is between 15 and 60 amino acid residues in length. In one embodiment, the HIV fusion inhibitor peptide further comprises a N-terminal group or C-terminal group, or both; those terminal groups may include, but are not limited to: an amino group or an acetyl group at the N-terminus; and a carboxyl group or an amido group at the C-terminus. In one embodiment, the HIV fusion inhibitor peptide may self-associate to form a dimer or a multimer, e.g., a trimer, or be synthesized in multimeric form, e.g., as a trimer.

Moreover, the present invention extends to a method of enhancing one or more biological properties in a peptide derived from the HR2 region of HIV gp41, and more preferably derived from a base amino acid sequence of SEQ ID NO:5, wherein the method comprises producing an HIV fusion inhibitor peptide having an amino acid sequence similar to SEQ ID NO:5, except that the HIV fusion inhibitor peptide amino acid sequence: (a) has more than one leucine zipper-like motif, and has at least one additional leucine other than a leucine needed to form a leucine zipper-like motif (i.e., other than at position 1 or 8 of a leucine zipper-like motif); or (b) has more than two leucine zipper-like motifs; and wherein the HIV fusion inhibitor peptide and preferably demonstrates an improvement in one or more biological properties. In certain embodiments, the HIV fusion inhibitor peptide is between 15 and 60 amino acid residues in length. In one embodiment, the HIV fusion inhibitor peptide further comprises a N-terminal group or C-terminal group, or both; those terminal groups may include, but are not limited to: an amino group or an acetyl group at the N-terminus; and a carboxyl group or an amido group at the C-terminus. In one embodiment, the HIV fusion inhibitor peptide may self-associate to form a dimer or multimer, e.g., a trimer, or be synthesized in multimeric form, e.g., as a trimer.

Preferably, the one or more biological properties that are demonstrated to be improved by an HIV fusion inhibitor peptide according to the present invention (as compared to a base amino acid sequence) may be selected from the group consisting of: biological half-life (e.g., enabling the HIV fusion inhibitor peptide to survive longer in vivo before being degraded in and/or removed from the bloodstream), solubility in an aqueous solution, stability in an aqueous solution, more potency (more potent antiviral activity) against HIV strains that have developed resistance to synthetic peptides derived from the natural sequence of HIV gp41 HR2 region (e.g., SEQ ID NO:2), and a combination thereof.

Also provided is a pharmaceutical composition or medicament comprising an HIV fusion inhibitor peptide according to the present invention and at least one additional component comprising a pharmaceutically acceptable carrier, a macromolecule, or a combination thereof.

The present invention also provides methods of using an HIV fusion inhibitor peptide according to the present invention. In one embodiment, an HIV fusion inhibitor peptide is used as a part of a therapeutic regimen containing one or more additional antiviral agents. Such therapeutic regimen is used for the therapy of HIV infection. In another embodiment, provided is a method of using an HIV fusion inhibitor peptide according to the present invention for inhibition of transmission of HIV to a target cell, comprising adding to the virus and the cell an amount of an HIV fusion inhibitor peptide, according to the present invention, effective to inhibit infection of the cell by the virus. This method may be used to treat HIV-infected individuals. In a preferred embodiment, inhibiting transmission of HIV to a target cell comprises inhibiting gp41-mediated fusion of HIV-1 to a target cell and/or inhibiting syncytia formation between an HIV-infected cell and a target cell. The present invention also provides for a method of treating HIV infection (preferably, HIV-1 infection) comprising administering to an HIV-infected individual a pharmaceutical composition comprising an HIV fusion inhibitor peptide according to the present invention. Preferably, the pharmaceutical composition is in an amount effective to inhibit transmission of HIV to a target cell, and/or in an amount effective to inhibit gp41-mediated fusion of HIV to a target cell. Also provided is a method for inhibiting HIV fusion comprising contacting the virus in the presence of a cell with an amount of an HIV fusion inhibitor peptide according to the present invention effective to inhibit HIV fusion. These methods may be used to treat HIV-infected individuals.

The present invention also provides the use of an HIV fusion inhibitor peptide according to the present invention, in the manufacture of a medicament for use in therapy of HIV infection (e.g., used in a method of inhibiting transmission of HIV, a method of inhibiting HIV fusion, and/or a method of treating HIV infection), as described herein. The medicament is preferably in the form of a pharmaceutical composition comprising an HIV fusion inhibitor peptide according to the present invention together with a pharmaceutically acceptable carrier.

The HIV fusion inhibitor peptides of the invention can routinely be produced via well-known methods, including the recombinant expression of nucleic acids encoding the peptide. For example, cells engineered to recombinantly express an HIV fusion inhibitor peptide can be cultured for an appropriate time and under appropriate conditions such that the peptide is expressed, and the peptide can be obtained therefrom.

The present invention also provides isolated nucleic acid molecules that encode an HIV fusion inhibitor peptide of the invention, as well as vectors, including expression vectors, comprising such nucleic acid molecules. The present invention also provides cells, e.g., *E. coli* or mammalian cells, comprising such vectors, wherein the cells can express the nucleic acid to produce the HIV fusion inhibitor peptide.

The HIV fusion inhibitor peptides of the invention can also, for example, be produced via synthesis methods. For example, also provided are specific peptide fragments, each peptide fragment capable of serving as an intermediate that may be covalently coupled with one or more other peptide fragments in a group of peptide fragments to yield a HIV fusion inhibitor peptide having an amino acid sequence of either SEQ ID NO:9, SEQ ID NO:10, SEQ ID NO:11, SEQ ID NO:12, SEQ ID NO:13, SEQ ID NO:14, or SEQ ID NO:15. In a preferred embodiment, the peptide fragments, within a group of peptide fragments according to the present invention, are coupled in a solution phase process in a manner to result in the desired HIV fusion inhibitor peptide having an amino acid sequence of SEQ ID NO:9, SEQ ID NO:10, SEQ ID NO:11, SEQ ID NO:12, SEQ ID NO:13, SEQ ID NO:14, or SEQ ID NO:15. Also provided is a method of producing an HIV fusion inhibitor peptide comprising synthesizing its constituent peptide fragments, and then assembling the peptide fragments to form the HIV fusion inhibitor peptide, wherein the HIV fusion inhibitor peptide has an amino acid sequence of either SEQ ID NO:9, SEQ ID NO:10, SEQ ID NO:11, SEQ ID NO:12, SEQ ID NO:13, SEQ ID NO:14, or SEQ ID NO:15. In one embodiment, synthesis methods are used to form a dimer or multimer of the HIV fusion inhibitor peptide, e.g., a trimer. In one embodiment, recombinant methods and/or linking are used to form a dimer or multimer of the HIV fusion inhibitor peptide. In one embodiment, a multimer formed of the HIV fusion inhibitor peptide is a linear multimer; in another embodiment, the multimer formed is non-linear, e.g., an aggregate.

The above and other objects, features, and advantages of the present invention will be apparent in the following Detailed Description of the Invention when read in conjunction with accompanying drawings.

5. BRIEF DESCRIPTION OF THE DRAWINGS

FIG. 2 shows a comparison of the natural amino acid sequences contained within the HR2 region of HIV-1 gp41 for purposes of illustration, and not limitation, as determined from various laboratory strains and clinical isolates, wherein illustrated are some of the variations in amino acid sequence (e.g., polymorphisms), as indicated by the single letter amino acid code.

6. DETAILED DESCRIPTION OF THE INVENTION

Definitions

Figure 1:
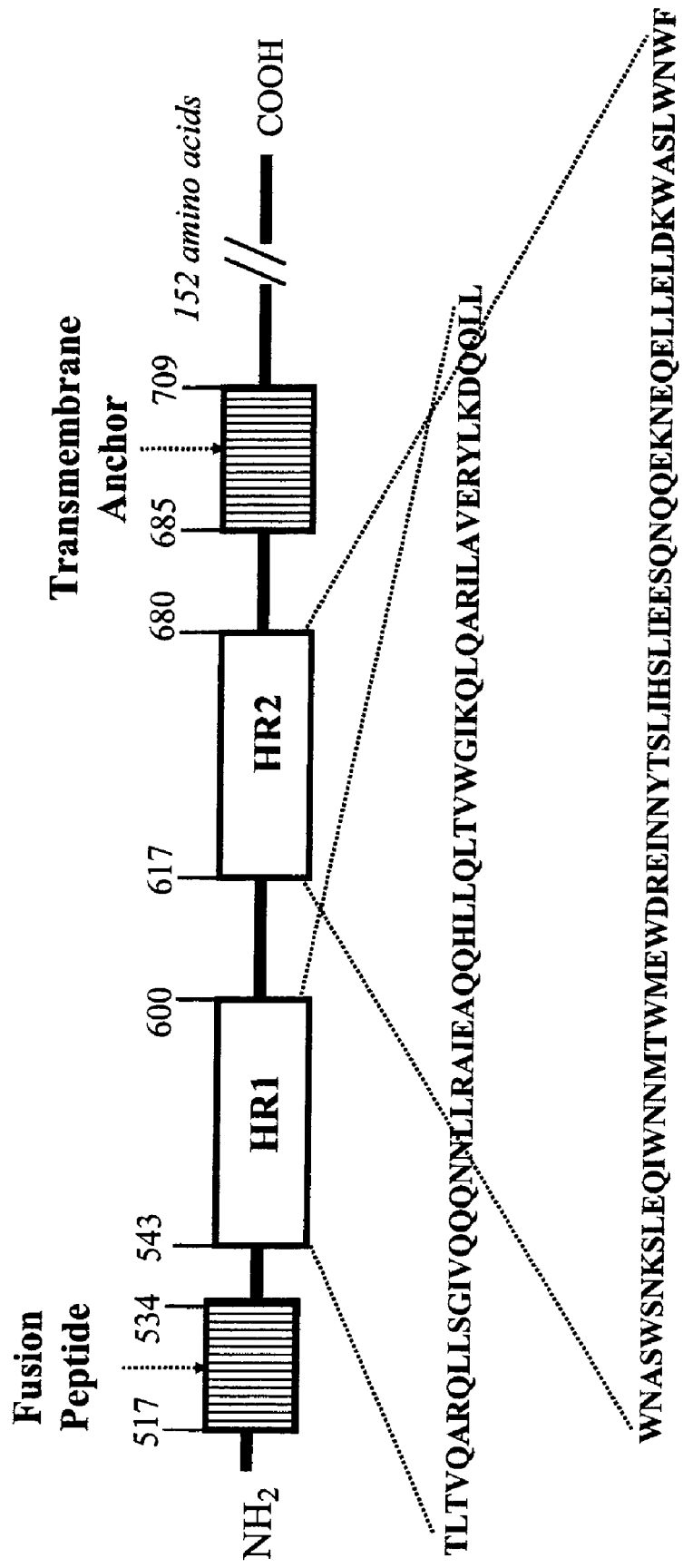
FIG. 1 is a schematic of HIV-1 gp41 showing the heptad repeat 1 region (HR1) and heptad repeat 2 region (HR2), along with other functional regions of gp41. Exemplary natural amino acid sequences corresponding to HR1 and HR2, and the amino acid position numbering, are shown for purposes of illustration and in relation to gp160, strain HIV$_{IIIB}$.

The term "individual," when used herein for purposes of the specification and claims, means a mammal, and preferably a human.

The term "target cell," when used herein for purposes of the specification and claims, means a cell capable of being infected by HIV. Preferably, the cell is a human cell or are human cells; and more preferably, human cells capable of being infected by HIV via a process, including membrane fusion.

The term "pharmaceutically acceptable carrier," when used herein for purposes of the specification and claims, means a carrier medium that does not significantly alter the biological activity of the active ingredient (e.g., an HIV fusion inhibitor peptide according to the present invention) to which it is added. A pharmaceutically acceptable carrier includes, but is not limited to, one or more of water, buffered water, saline, 0.3% glycine, aqueous alcohols, isotonic aqueous solution; and may further include one or more substances, such as glycerol, oils, salts, such as sodium, potassium, magnesium and ammonium, phosphonates, carbonate esters, fatty acids, saccharides (e.g., mannitol), polysaccharides, polymers, excipients, and preservatives and/or stabilizers (to increase shelf-life or as necessary and suitable for manufacture and distribution of the composition). Preferably, the pharmaceutically acceptable carrier is suitable for intravenous, intramuscular, subcutaneous or parenteral administration.

By the term "an amino acid comprising isoleucine or leucine," unless otherwise specifically pointed out, what is meant for purposes of the specification and claims and in reference to an HIV fusion inhibitor peptide according to the present invention, is to refer to isoleucine or leucine, respectively, or their respective naturally occurring amino acid (e.g., L-amino acid), non-naturally occurring amino acid (e.g., D-amino acid), isomeric form (e.g., norleucine, allo-isoleucine, and the like) or to a derivative form (e.g., tert-leucine). A preferred form of an amino acid isoleucine or leucine may be used to the exclusion of forms of the amino acid other than the preferred form of the amino acid. The HIV fusion inhibitor peptide according to the present invention may also comprise, in its amino acid sequence, one or more polymorphisms found in the sequence of the HR2 region of the HIV gp41 from which it is derived (see, e.g., FIG. 2), except at the one or more positions of the amino acid sequence taught herein to include an amino acid comprising isoleucine or leucine.

The term "HIV" refers to Human Immunodeficiency Virus, and more preferably HIV-1.

The term "isolated" when used in reference to an HIV fusion inhibitor peptide, or a peptide fragment, according to the present invention, means that it is substantially free of components which have not become part of the integral structure of the peptide itself, e.g., such as substantially free of chemical precursors or other chemicals when chemically synthesized, produced, or modified using biological, biochemical, or chemical processes.

The term "between 1 to 3 amino acid substitutions" when used in reference to an HIV fusion inhibitor peptide according to the present invention, means that an HIV fusion inhibitor peptide according to the present invention may also have the amino acid sequence of any one of SEQ ID NOs:9-15, except that there is not less than one and not more than three amino acid differences compared to any one of SEQ ID NOs:9-15; while yet still having either: (a) more than one leucine zipper-like motif, and at least one additional leucine other than a leucine needed to form a leucine zipper-like motif (i.e., other than at position 1 or 8 of a leucine zipper-like motif), or (b) between 3 and 5 leucine zipper-like motifs; and having antiviral activity against HIV (activity in inhibiting HIV-mediated fusion). In that regard, the amino acid differences of an HIV fusion inhibitor peptide having substitutions (when compared to SEQ ID NOs:9-15) are in positions of the amino acid sequence other than the leucine and/or isoleucine residues denoted for HIV fusion inhibitor peptides according to the present invention (see, e.g., illustrations (I) and (II) herein). The not less than one and not more than 3 amino acid differences include, but are not limited to, a conservative amino acid substitution (known in the art to include substitutions of amino acids having substantially the same charge, size, hydrophilicity, and/or aromaticity as the amino acid replaced; examples including, but are not limited to, glycine-alanine-valine, tryptophan-tyrosine, aspartic acid-glutamic acid, arginine-lysine, asparagine-glutamine, and serine-threonine) and/or polymorphisms (e.g., as illustrated in FIG. 2, or as found in laboratory, various clades, and/or clinical isolates of HIV-1). For example, as related to SEQ ID NOs: 11, 12, or 13, an HIV fusion inhibitor peptide has between one to 3 amino acid differences that are in positions other than amino acid residues 10, 17, 24, 31, and 38 of any one of SEQ ID NOs:11, 12, or 13. For example, as related to SEQ ID NO:9 and SEQ ID NO:14, an HIV fusion inhibitor peptide has between one to 3 amino acid differences that are in positions other than amino acid residues 10, 17, 21, 24, and 38 of SEQ ID NO:9 or of SEQ ID NO:14. For example, as related to SEQ ID NO:10 or SEQ ID NO:15, an HIV fusion inhibitor peptide has between one to 3 amino acid differences that are in positions other than amino acid residues 10, 17, 21, 31, and 38 of SEQ ID NO:10 or SEQ ID NO:15. An illustrative example of this embodiment includes, but is not limited to, an amino acid sequence of SEQ ID NO:16, wherein a position that may be the site of an amino acid difference of the between one and three amino acid substitutions is denoted by Xaa (representing any amino acid, naturally or non-naturally occurring; i.e., more than one possible amino acid may be used in this amino acid position). Also, one or more conservative amino acid substitutions can be made, such as a lysine substituted by an arginine or histidine, an arginine substituted by a lysine or histidine, a glutamic acid substituted by an aspartic acid, or an aspartic acid substituted by a glutamic acid. Amino acid positions 10, 17, 21, 24, 31, and 38 are underlined for illustrative purposes. In also referring to SEQ ID NOs:9-15, note that in SEQ ID NO:16 "Zaa" is used to denote an amino acid that may be either leucine or isoleucine; and Baa is used to denote an amino acid that is preferably either leucine, isoleucine, but may be Xaa, except that at least one Baa is either a leucine or isoleucine.

```
SEQ ID NO: 16:
XaaXaaXaaEAXaaDRAZaaAEXaaAARZaaEAZaaZaaRABaaXaaEXa aXaaEKBaaEAAZaaREZaa
```

In one embodiment, an HIV fusion inhibitor peptide corresponding to the requirements of SEQ ID NO:16 has a isoleucine or leucine at each of amino acid positions 3, 10, 17, 24, 31 and/or 38 such that the peptide exhibits 2, 3, 4 or 5 leucine zipper-like motifs. In another embodiment, peptide also has a non-leucine zipper motif leucine or isoleucine, preferably leucine, at position 21 of the peptide. The HIV fusion inhibitor peptides of the invention can also include peptides derived from the HR2 region of HIV gp41 corresponding to SEQ ID NO:5 (by sequence alignment) present in laboratory, clades or clinical isolates of HIV-1, as long as the HIV fusion inhibitor peptides satisfy the amino acid requirements of SEQ ID NO:16. In one embodiment, such HIV fusion inhibitor peptides exhibit from between 1 to 3 amino acid substitutions, compared to any of SEQ ID NOs:9-15. In certain embodiments, the HIV fusion inhibitor peptide is between 15 and 60 amino acid residues in length. In one embodiment, the HIV fusion inhibitor peptide further comprises a N-terminal group or C-terminal group, or both; and those terminal groups may include, but are not limited to: an amino group or an acetyl group at the N-terminus; and a carboxyl group or an amido group at the C-terminus. In one embodiment, the HIV fusion inhibitor peptide may self-associate to form a dimer or multimer, e.g., a trimer, or, for example, may be synthesized, expressed or linked in dimeric or multimeric form, e.g., as a trimer.

The HIV fusion inhibitor peptides of the invention can also include peptides exhibiting the variant amino acid sequences of any of the peptides disclosed in US 2006/0247416, the entire contents of which is incorporated herein by reference in its entirety, as long as the HIV fusion inhibitor peptides satisfy the amino acid requirements of SEQ ID NO:16. In one embodiment, such HIV fusion inhibitor peptides exhibit from between 1 to 3 amino acid substitutions compared to any one of SEQ ID NOs:9-15. In certain embodiments, the HIV fusion inhibitor peptide is between 15 and 60 amino acid residues in length. In one embodiment, the HIV fusion inhibitor peptide further comprises a N-terminal group or C-terminal group, or both; and those terminal groups may include, but are not limited to: an amino group or an acetyl group at the N-terminus; and a carboxyl group or an amido group at the C-terminus. In one embodiment, the HIV fusion inhibitor peptide may self-associate to form a dimer or multimer, e.g., a trimer, or, for example, may be synthesized, expressed or linked in dimeric or multimeric form, e.g., as a trimer.

The term "reactive functionality," when used herein for purposes of the specification and claims, means a chemical group or chemical moiety that is capable of forming a bond with another chemical group or chemical moiety. With respect to chemical groups, a reactive functionality is known to those skilled in the art to comprise a group that includes, but is not limited to, maleimide, thiol, carboxylic acid, hydrogen, phosphoryl, acyl, hydroxyl, acetyl, hydrophobic, amine, amido, dansyl, sulfo, a succinimide, a thiol-reactive, an amine-reactive, a carboxyl-reactive, and the like. A preferred reactive functionality may be used, in application to the present invention, to the exclusion of a reactive functionality other than the preferred reactive functionality.

The term "linker," when used herein for purposes of the specification and claims, means a compound or moiety that acts as a molecular bridge to operably link two different molecules (e.g., a first reactive functionality of a linker is covalently coupled to a reactive functionality of a macromolecular carrier, and a second reactive functionality of the linker is covalently coupled to a reactive functionality of an HIV fusion inhibitor peptide). The linker may be amino acids, as in production of a recombinant fusion protein containing one or more copies of the HIV fusion inhibitor peptide according to the present invention. Alternatively, the two different molecules may be linked to the linker in a step-wise manner (e.g., via chemical coupling). In general, there is no particular size or content limitations for the linker so long as it can fulfill its purpose as a molecular bridge. Linkers are known to those skilled in the art to include, but are not limited to, chemical chains, chemical compounds (e.g., reagents), amino acids, and the like. The linkers may include, but are not limited to, homobi-functional linkers, heterobifunctional linkers, biostable linkers, hydrolysable linkers, and biodegradable linkers, as well known in the art. Heterobifunctional linkers, well known to those skilled in the art, contain one end having a first reactive functionality to specifically link a first molecule, and an opposite end having a second reactive functionality to specifically link to a second molecule. It will be evident to those skilled in the art that a variety of monofunctional, difunctional, and polyfunctional reagents (such as those described in the catalog of the Pierce Chemical Co., Rockford, Ill.) may be employed as a linker with respect to the present invention. Depending on such factors as the molecules to be linked, the conditions in which the linking is performed, and the intended pharmacokinetic properties upon administration, the linker may vary in length and composition for optimizing such properties as: preservation of biological activity and function, stability, resistance to certain chemical and/or temperature parameters, susceptibility to cleavage in vivo, and of sufficient stereo-selectivity or size.

The term "macromolecular carrier," when used herein for purposes of the specification and claims, means a molecule which is linked, joined, or fused (e.g., chemically, or through recombinant means using genetic expression) to one or more peptides according to the present invention, whereby the molecule is capable of conferring one or more properties of: stability to the one or more peptides, increase in biological activity of the one or more peptides, or an increase in plasma half-life of the one or more peptides (e.g., prolonging the persistence of the one or more peptides in the body) relative to that with respect to the one or more peptides in the absence of the molecule. Such macromolecular carriers are well known in the art to include, but are not limited to, serum proteins, polymers, carbohydrates, and lipid-fatty acid conjugates. Serum proteins typically used as macromolecular carriers include, but are not limited to, transferrin, albumin (preferably human), immunoglobulins (preferably human IgG or one or more chains thereof), or hormones. Polymers typically used as macromolecular carriers include, but are not limited to, polylysines or poly(D-L-alanine)-poly(L-lysine)s, or polyols. A preferred polyol comprises a water-soluble poly (alkylene oxide) polymer, and can have a linear or branched chain(s). A preferred polymer is a branched chain polyol (such as a PEG, having multiple (for example, 3 or more) chains, each which may be coupled to the HIV fusion inhibitor peptide directly or via a linker); and more preferably, a branched chain polyol that is biodegradable, and/or cleaved over time, under in vivo conditions. Suitable polyols include, but are not limited to, polyethylene glycol (PEG), polypropylene glycol (PPG), and PEG-PPG copolymers. A preferred polyol comprises PEG having an average molecular size selected from the range of from about 1,000 Daltons to about 20,000 Daltons. Other types of macromolecular carriers that can be used, which generally have molecular weights higher than 20,000 Daltons, are known in the art.

The term "chemical protecting group," or "CPG," when used herein for purposes of the specification and claims, means a chemical moiety that is used to block a reactive functionality comprising an amine group from chemically reacting with another reactive functionality. Chemical protecting groups are well known by those in the art of peptide synthesis to include, but are not limited to, tBu (t-butyl), trt (triphenylmethyl(trityl)), OtBu (tert-butoxy), Boc or t-Boc (tert-butyloxycarbonyl), Fmoc (9-fluorenylmethoxycarbonyl), Aoc (t-amyloxy-carbonyl), TEOC (β-trimethylethyloxycarbonyl), CLIMOC (2-chloro-1-indanyl methoxyl carbonyl), BIMOC (benz-[f]-indene-3-methoxyl carbonyl), PBF (2,2,4,6,7-pentamethyldihydrobenzofuan-5-sulfonyl), 2-Cl—Z (chlorobenzyl-oxycarbonyl), Alloc (allyloxycarbonyl), Cbz (benzyloxycarbonyl), Adoc (adamantyloxy-carbonyl), Mcb (1-methylcyclobutyloxycarbonyl), Bpoc (2-(p-biphenylyl) propyl-2-oxycarbonyl), Azoc (2-(p-phenylazophenyl) propyl-2-oxycarbonyl), Ddz (2,2 dimethyl-3,5-dimethyloxybenzyl-oxycarbonyl), MTf (4-methoxy-2,3,6-trimethoylbenzenesulfonyl), PMC (2,2,5, 7,8-pentamethylchroman-6-sulfonyl), Tos (tosyl), Hmb (2-hydroxyl-4-methoxybenzyl), Poc (2-phenylpropyl-2-oxycarbonyl), Dde (1-(4,4-dimethyl-2,6-dioxocyclohex-1-ylidene)ethyl), ivDde (1-(4,4-dimethyl-2,6-dioxo-cyclohex-1-ylidene)-3-methylbutyl), benzyl, dansyl, para-nitrobenzyl ester, and the like. A preferred chemical protecting group may be used, in application to the present invention, to the exclusion of a chemical protecting group other than the preferred chemical protecting group.

The term "deprotection," when used herein for purposes of the specification and claims, is known in the art to mean a process by which one or more chemical protecting group(s) is removed from a molecule containing one or more chemical protecting groups, wherein the molecule comprises an amino acid, peptide fragment, or HIV fusion inhibitor peptide according to the present invention. Generally, the deprotection process involves reacting the molecule protected by one or more chemical protecting groups with a chemical agent that removes the chemical protecting group. For example, an N-terminal alpha amino group, which is protected by a chemical protecting group, may be reacted with a base to remove base labile chemical protecting groups (e.g., Fmoc, and the like). Chemical protecting groups (e.g., Boc, TEOC, Aoc, Adoc, Bopc, Ddz, Cbz, and the like) are removed by acid. Other chemical protecting groups, particularly those derived from carboxylic acids, may be removed by acid or a base.

The terms "first," "second," "third," and the like, may be used herein to: (a) indicate an order; or (b) to distinguish between molecules or reactive functionalities of a molecule; or (c) a combination of (a) and (b). However, the terms "first," "second," "third," and the like, are not otherwise to be construed as limiting the invention.

The terms "peptide fragment" and "intermediate" are used synonymously herein, in relation to an HIV fusion inhibitor peptide according to the present invention, and for the purposes of the specification and claims, to mean a peptide comprising an amino acid sequence of no less than about 5 amino acids and no more than about 30 amino acid residues in length, and comprises at least a portion (as contiguous amino acids) of the amino acid sequence of that HIV fusion inhibitor peptide. See Examples 4-7, and Tables 4, 5, 7 & 8 herein, for illustrative examples of peptide fragments useful for making SEQ ID NOs:9 and 10. Further, while in a preferred embodiment peptide fragments (singly or when combined as a group to form an HIV fusion inhibitor peptide) are synthesized such that peptidic bonds are formed between the amino acid residues, it is readily apparent to one skilled in the art that non-peptidic bonds may be formed using reactions known to those skilled in the art (e.g., imino, ester, hydrazide, azo, semicarbazide, and the like).

The term "pharmacokinetic properties," when used herein for purposes of the specification and claims, means the total amount of active ingredient (e.g., HIV fusion inhibitor peptide according to the present invention) in a pharmaceutical composition that is systematically available over time. Pharmacokinetic properties may be determined by measuring total systemic concentrations of the HIV fusion inhibitor peptide over time after being administered in vivo. As an example, pharmacokinetic properties may be expressed in terms of the Area Under the Curve (AUC), biological half-life, and/or clearance. AUC is the integrated measure of systemic active ingredient concentrations over time in units of mass-time/volume. Following the administration of a dose of active ingredient, the AUC from the time of dosing to the time when no active ingredient remains in the body, is a measure of the exposure of the individual to the active ingredient (and/or a metabolite of an active ingredient). An HIV fusion inhibitor peptide according to the present invention has "improved" or "increased" pharmacokinetic properties when it has one or more of (a) a longer ("increase") in biological (terminal elimination) half life ("t½"), and (b) a reduction in biological (total body) clearance (Cl), as compared to that of an HIV fusion inhibitor peptide other than an HIV fusion inhibitor peptide according to the present invention (see, e.g., Tables 1 and 2 in Example 2 herein). In a preferred embodiment, improved pharmacokinetics may mean a clearance that is reduced, relative to that of a compared peptide, such as typically being from about 2 fold reduction to about 10 fold reduction. In another preferred embodiment, improved pharmacokinetics may mean an increase in biological half-life of from about a 10% increase to about a 60% increase relative to that of a peptide subjected to comparison. Improved pharmacokinetics may also encompass both a reduction in clearance and an increase in biological half-life. The equations used to calculate area-under the plasma concentration vs. time curve (AUC), total body clearance (Cl), and terminal elimination half-life (t½) are set forth herein in Example 1.

The term "in solution," as standard in the art in referring to an aqueous fluid into which is dissolved one or more solids, is used herein for the purposes of the specification and claims to mean an aqueous solution containing the HIV fusion inhibitor peptide dissolved therein under realistic use conditions of concentration and temperature as described herein in more detail and as standard in the art for an injectable drug formulation. There are various ways known in the art to distinguish formation of a solution, as opposed to formation of a suspension, such as checking for visual clarity (transparency of a solution versus cloudiness of a suspension), light transmission, and the like. "Solubility" is determined by the amount (e.g., weight percent) of HIV fusion inhibitor peptide that is present in solution in an aqueous fluid without showing observed evidence of precipitation out of solution, or gelling of the aqueous fluid containing the HIV fusion inhibitor peptide. "Stability" is determined by the amount of HIV fusion inhibitor peptide, in solution, that degrades over time.

The terms "treatment" or "therapy," are used interchangeably with respect to HIV infection, and for purposes of the specification and claims, to mean that an HIV fusion inhibitor peptide (or a pharmaceutical composition having the HIV fusion inhibitor peptide as an active drug substance) may be used to affect one or more processes associated with HIV infection, or one or more parameters or endpoints used as indicators for determining the therapeutic effect of such treatment or therapy (e.g., "therapeutic application"). For example, the HIV fusion inhibitor peptide may be used to inhibit one or more of the following processes: transmission of HIV to a target cell; fusion between HIV and a target cell ("HIV fusion"); viral entry (the process of HIV or its genetic material entering into a target cell during the infection process); and syncytia formation (e.g., fusion between an HIV-infected cell and a target cell). Viral suppression (determined by methods known in the art for measuring the viral load of HIV in a body fluid or tissue) is a commonly used primary endpoint, and an increase in the number of $CD4^+$ cells circulating in the bloodstream is a commonly used secondary endpoint, for assessing the efficacy of a drug in treatment or therapy of HIV infection; each being a measurable effect of inhibiting transmission of HIV to a target cell. Thus, an HIV fusion inhibitor peptide according to the present invention may be used to effect a therapeutic application comprising viral suppression and/or an increase in the relative number of circulating $CD4^+$ cells.

The present invention is directed to an HIV fusion inhibitor peptide which is similar in amino acid sequence to a base amino acid sequence of SEQ ID NO:5 except that, as compared to the base amino acid sequence, the HIV fusion inhibitor peptide amino acid sequence has: (a) more than one leucine zipper-like motif in its amino acid sequence; and (b) at least one additional leucine other than a leucine needed to form a leucine zipper-like motif (i.e., other than at position 1 or 8 of a leucine zipper-like motif); wherein the HIV fusion inhibitor peptide demonstrates an improvement in one or more biological properties. More particularly, the present invention relates to amino acid sequences of peptides exemplified by SEQ ID NOs:9, 10, 14, and 15, or an HIV fusion inhibitor peptide containing between one to three amino acid differences as compared to any one of SEQ ID NOs:9, 10, 14, and 15; their use as HIV fusion inhibitor peptides and in pharmaceutical compositions; and peptide fragments and methods of synthesis to obtain these HIV fusion inhibitor peptides. In another embodiment of the present invention, the present invention is also directed to an HIV fusion inhibitor peptide which is similar in amino acid sequence to a base amino acid sequence of SEQ ID NO:5, except that, as compared to the base amino acid sequence, the HIV fusion inhibitor peptide amino acid sequence has more than two leucine zipper-like motifs in its amino acid sequence; wherein the HIV fusion inhibitor peptide demonstrates an improvement in one or more biological properties. More particularly, the present invention relates to amino acid sequences of peptides exemplified by SEQ ID NOs:11-13, or an HIV fusion inhibitor peptide containing between one to three amino acid differences as compared to any one of SEQ ID NOs:11-13; their use as HIV fusion inhibitor peptides and in pharmaceutical compositions; and peptide fragments and methods of synthesis to obtain these HIV fusion inhibitor peptides.

Example 1

In the following examples, various biophysical parameters and biological parameters were assessed. The general methodologies for determining these parameters are as follows.

Peptides, including HIV fusion inhibitor peptides according to the present invention and base sequences, were synthesized on a peptide synthesizer using standard solid phase synthesis techniques and using standard FMOC peptide chemistry, or a combination of solid phase synthesis and solution phase synthesis as described in more detail in Example 4 herein. In this example, the HIV fusion inhibitor peptides may further comprise reactive functionalities; i.e., most were blocked at the N-terminus by an acetyl group and/or at the C-terminus by an amide group. After cleavage from the resin, the peptides were precipitated, and the precipitate was lyophilized. The peptides were then purified using reverse-phase high performance liquid chromatography; and peptide identity was confirmed with electrospray mass spectrometry.

Assessment of biophysical parameters included measurement of helicity and thermal stability. Helicity was assessed by circular dichroism ("CD") as follows. Briefly, CD spectra were obtained using a spectrometer equipped with a thermoelectric temperature controller. The spectra was obtained at 25° C. with 0.5 nanometer (nm) steps from 200 to 260 nm, with a 1.5 nm bandwidth, and a typical averaging time of 4 seconds/step. After the cell/buffer blank was subtracted, spectra were smoothed using a third-order least-squares polynomial fit with a conservative window size to give random residuals. Raw ellipticity values were converted to mean residue ellipticity using standard methods, and plotted was the wavelength (from 200 to 260 nm) versus $[\theta] \times 10^{-3}$ (degrees $cm^2$/dmol). Percent helicity values were then calculated using standard methods (usually expressed as percent helicity at 10 μM, 25° C.). Assessment of thermal stability was performed by monitoring the change in CD signal at 222 nm as temperature was raised in 2° C. steps, with 1 minute equilibration times. The stability for each sample (e.g., HIV fusion inhibitor peptide), as represented by the Tm value, is the temperature corresponding to the maximum value of the first derivative of the thermal transition.

Assessment of biological properties included measurement of antiviral activity against HIV-1 strains. In determining antiviral activity (e.g., one measure being the ability to inhibit transmission of HIV to a target cell) of the HIV fusion inhibitor peptides according to the present invention, used was an in vitro assay which has been shown, by data generated using peptides derived from the HR regions of HIV gp41, to be predictive of antiviral activity observed in vivo. More particularly, antiviral activity observed using an in vitro infectivity assay ("Magi-CCR5 infectivity assay"; see, e.g., U.S. Pat. No. 6,258,782) has been shown to reasonably correlate to antiviral activity observed in vivo for the same HIV gp41 derived peptides (see, e.g., Kilby et al., 1998, Nature Med. 4:1302-1307). These assays score for reduction of infectious virus titer employing the indicator cell lines MAGI or the CCR5 expressing derivative cMAGI. Both cell lines exploit the ability of HIV-1 tat to transactivate the expression of a β-galactosidase reporter gene driven by the HIV-LTR. The β-gal reporter has been modified to localize in the nucleus and can be detected with the X-gal substrate as intense nuclear staining within a few days of infection. The number of stained nuclei can thus be interpreted as equal to the number of infectious virions in the challenge inoculum if there is only one round of infection prior to staining. Infected cells are enumerated using a CCD-imager and both primary and laboratory adapted isolates show a linear relationship between virus input and the number of infected cells visualized by the imager. In the MAGI and CMAGI assays, a 50% reduction in infectious titer (Vn/Vo=0.5) is significant, and provides the primary cutoff value for assessing antiviral activity ("IC50" is defined as the concentration of active ingredient resulting in a 50% reduction in infectious virus titer). Peptides tested for antiviral activity were diluted into various concentrations, and tested in duplicate or triplicate against an HIV inoculum adjusted to yield approximately 1500-2000 infected cells/well of a 48 well microtiter plate. The peptide (in the respective dilution) was added to the CMAGI or MAGI cells, followed by the virus inocula; and 24 hours later, an inhibitor of infection and cell-cell fusion (e.g., T20 (SEQ ID NO:2; enfuvirtide)) was added to prevent secondary rounds of HIV infection and cell-cell virus spread. The cells were cultured for 2 more days, and then fixed and stained with the X-gal substrate to detect HIV-infected cells. The number of infected cells for each control and peptide dilution was determined with the CCD-imager, and then the IC50 was calculated (expressed in μg/ml).

Viruses resistant to the antiviral activity of a peptide consisting of a base sequence can be produced using standard laboratory methods. Basically, after calculating the IC50 and IC90, cells were mixed with virus and the peptide (e.g., at a concentration close to the IC90) in culture (including when the cells are split thereafter). The cultures are maintained and monitored until syncytia are present. Virus harvested from this first round of culture is used to infect cells in a second round of culture, with the peptide present in a higher concentration (2 to 4 times) than that used in the first round of culture. The second round of culture is maintained and monitored for presence of virus resistant to the antiviral activity of the peptide. Subsequent rounds of culture may be needed to finally generate a viral isolate resistant to the antiviral activity of the peptide (at a pre-determined level of the IC50 of the peptide against such isolate).

For determining pharmacokinetic properties, an HIV fusion inhibitor peptide or a base sequence from which an HIV fusion inhibitor peptide is derived was dosed intravenously in cynomolgus monkeys (*Macaca fasicularis*) (other animal models may be used for determining pharmacokinetic properties, as known in the art). At various times post-dose, blood samples were drawn and plasma isolated by centrifugation. Plasma samples were stored frozen until analysis by LC-MS (liquid chromatography/mass spectrometry) in the electrospray, positive-ion mode. An HIV fusion inhibitor or base sequence was eluted from a C18 or C8 HPLC column with a gradient of acetonitrile in a buffer of 10 mM ammonium acetate, pH 6.8. At the time of analysis, plasma samples were deproteinated with either two or three volumes of acetonitrile containing 0.5% formic acid. Duplicate calibration standards in cynomolgus plasma samples were prepared at the same time as the samples and analyzed before and after the samples containing either HIV fusion inhibitor peptide or base sequence. Pharmacokinetic properties were calculated from the plasma concentration-time data using either mono-exponential or bi-exponential mathematical models. Models were derived by non-linear least squares optimization. A $1/C^2$ weighting of concentrations was used. The following equations were used to calculate area-under the plasma concentration vs. time curve (AUC), total body clearance (Cl), and terminal elimination half-life (t½).

$$AUC = A/-a + B/-b$$

Where A and B are intercepts and a and b are the rate constants of the exponential equations describing the distribution and elimination phases, respectively. When mono-exponential models were used, the "A" and "a" properties were eliminated.

$$Cl = Dose/AUC \text{(expressed in L/K/hr)}$$

$$t\text{½} = -0.6903/b \text{(expressed in hr)}$$

Example 2

For purposes of illustrating the invention, the base sequence has the following amino acid sequence (SEQ ID NO:5):

TTWEAWDRAIAEYAARIEALIRAAQEQQEKNEAALREL

In one embodiment, an HIV fusion inhibitor peptide according to the present invention comprises, as compared to a base sequence from which it is derived, more than 2 leucine zipper-like motifs. Examples of such HIV fusion inhibitor peptides include, but are not limited to, SEQ ID NO:11, SEQ ID NO:12, and SEQ ID NO:13; or an amino acid sequence having between one and three amino acid differences as compared to (e.g., at least a 92% identity with) any one of SEQ ID NO:11, SEQ ID NO:12, SEQ ID or NO:13; each HIV fusion inhibitor peptide has an amino acid sequence of between 3 and 5 leucine zipper-like motifs. The following illustration (I) shows amino acid sequences of HIV fusion inhibitor peptides according to the present invention with amino acid differences (as compared to the base sequence) using the one letter amino acid code ("L" for leucine, and "I" for isoleucine) under the amino acid position of the base sequence (as aligned using an "|"), and with the isoleucine and leucines involved in a leucine zipper-like motif (either at position 1 or 8 of the same leucine zipper-like motif, or position 8 of one leucine zipper-like motif and position 1 of an adjacent leucine zipper-like motif) underlined. Position 1 or 8 of one leucine zipper may also function as the opposite terminal position of another leucine zipper-like motif in a sequence, i.e., as position 8 of one motif and position 1 of another subsequent motif.

(I)

```
TTWEAWDRAIAEYAARIEALIRAAQEQQEKNEAALREL   SEQ ID NO: 5
             |          |
             L          L              SEQ ID NO: 11
             I          L              SEQ ID NO: 12
             L          I              SEQ ID NO: 13
```

In another embodiment, an HIV fusion inhibitor peptide according to the present invention comprises, as compared to a base sequence from which it is derived, more than 1 leucine zipper-like motif, as well as an additional leucine not involved in formation of a leucine zipper-like motif. Examples of such HIV fusion inhibitor peptides include, but are not limited to, SEQ ID NO:9, SEQ ID NO:10, SEQ ID NO:14, and SEQ ID NO:15; or an amino acid sequence having between one and three amino acid differences as compared to (e.g., at least a 92% identity with) any one of SEQ ID NO:9, SEQ ID NO:10, SEQ ID NO:14, or SEQ ID NO:15; and each HIV fusion inhibitor peptide amino acid sequence differing from the base sequence of SEQ ID NO:5 by containing more than 1 leucine zipper-like motif, and an additional leucine not involved in formation of a leucine zipper-like motif (i.e., other than at position 1 or 8 of a leucine zipper-like motif). In one preferred embodiment, the non-leucine zipper-like motif leucine substitution replaces a isoleucine at the amino acid 21 position in the base sequence of SEQ ID NO:5. The following illustration (II) shows amino acid sequences of HIV fusion inhibitor peptides according to the present invention with amino acid differences (as compared to the base sequence) using the one letter amino acid code ("L" for leucine, and "I" for isoleucine) under the amino acid position of the base sequence (as aligned using an "|"), and with the isoleucine and leucines involved in a leucine zipper-like motif (either at position 1 or 8 of the same leucine zipper-like motif, or position 8 of one leucine zipper-like motif and position 1 of an adjacent leucine zipper-like motif) underlined. Italicized is a leucine not involved in formation of a leucine zipper-like motif.

(II)

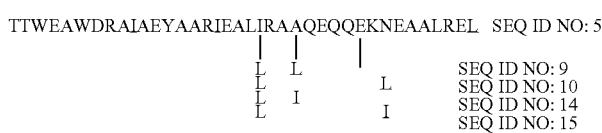

Illustration (III) presents the full sequences of the "base sequence" SEQ ID NO:5 and SEQ ID NOs:9-15. Amino acid substitutions in each of SEQ ID NOs:9-15 relative to the SEQ ID NO:5 base sequence are underlined and in bold.

(III)

```
                                                              SEQ ID NO: 5
T T W E A W D R A I A E Y A A R I E A L I R A A Q E Q Q E K N E A A L R E L

SEQ ID NO: 9
T T W E A W D R A I A E Y A A R I E A L L R A L Q E Q Q E K N E A A L R E L

SEQ ID NO: 10
T T W E A W D R A I A E Y A A R I E A L L R A A Q E Q Q E K L E A A L R E L

SEQ ID NO: 11
T T W E A W D R A I A E Y A A R I E A L I R A L Q E Q Q E K L E A A L R E L

SEQ ID NO: 12
T T W E A W D R A I A E Y A A R I E A L I R A I Q E Q Q E K L E A A L R E L

SEQ ID NO: 13
T T W E A W D R A I A E Y A A R I E A L I R A L Q E Q Q E K I E A A L R E L

SEQ ID NO: 14
T T W E A W D R A I A E Y A A R I E A L L R A I Q E Q Q E K N E A A L R E L

SEQ ID NO: 15
T T W E A W D R A I A E Y A A R I E A L L R A A Q E Q Q E K I E A A L R E L
```

With reference to Table 1, an HIV fusion inhibitor peptide according to this present invention was compared to synthetic peptides which have the same base sequence, but differ in amino acid sequence (as compared to SEQ ID NOs:9-15) and that have anti-HIV activity. The comparison includes biophysical parameters and biological activity parameters, as determined using the methodology described in Example 1 herein. In determining biological activity, as assessed by antiviral activity, a viral isolate is utilized which is resistant to the antiviral activity of some peptides known to inhibit HIV-mediated fusion (the resistant viral isolate being designated as "Res" in Table 1).

TABLE 1

Biophysical and Biological (antiviral activity) Parameters

| SEQ ID NO: | Helicity (%) | Tm (° C.) | Antiviral Activity (μg/ml) HIV-IIIB IC50 | Antiviral Activity (μg/ml) HIV-Res IC50 |
|---|---|---|---|---|
| 5 | 71 | 42 | <0.10 | <0.10 |
| 6 | 97 | 65 | <0.10 | ≧0.10 |
| 7 | 84 | 75 | <0.10 | >0.10 |
| 8 | 99 | 46 | <0.10 | Not tested |
| 9 | 61 | 62 | <0.10 | <0.10 |
| 10 | 77 | 75 | <0.10 | <0.10 |

SEQ ID NO:6 differs from SEQ ID NO:5 by a single substitution at position 24. SEQ ID NO:7 differs from SEQ ID NO:5 by a single substitution at position 31. These substitutions lead to an improvement in half-life (see Table 2, below). SEQ ID NO:6 is similar to an HIV fusion inhibitor peptide according to the present invention having SEQ ID NO:9, except that the amino acid sequence of SEQ ID NO:9 has one further amino acid difference, a leucine in amino acid position 21 (whereas SEQ ID NO:6 has an isoleucine in amino acid position 21). With reference to Table 1, the leucine for isoleucine substitution in SEQ ID NO:9 delivers a reduction (from 97% to 61%) in helicity, while maintaining antiviral activity, including a good resistance profile (activity against the resistant viral isolate "Res") as compared to a peptide of SEQ ID NO:6. Similarly, SEQ ID NO:7 is an amino acid sequence similar to an HIV fusion inhibitor peptide according to the present invention having SEQ ID NO:10, except that the amino acid sequence of SEQ ID NO:10 has one amino acid difference, a leucine in amino acid position 21 (whereas SEQ ID NO:7 has an isoleucine in amino acid position 21). With reference to Table 1, the leucine for isoleucine substitution in SEQ ID NO:10 results in a reduction (from 84% to 77%) in helicity, while maintaining antiviral activity, including a good resistance profile (activity against the resistant viral isolate "Res") as compared to a peptide of SEQ ID NO:7. Thus, Table 1 demonstrates improved properties for SEQ ID NO:9 and 10 relative to SEQ ID NOs:6-7.

Illustrated in this embodiment are pharmacokinetic properties of an HIV fusion inhibitor peptide according to the present invention as compared to a base amino acid sequence. Using methods for assessing pharmacokinetic properties as previously described in more detail in Example 1, Table 2 illustrates pharmacokinetic properties of the peptides of SEQ ID NOs:5-10.

TABLE 2

| SEQ ID NO: | Clearance (L/kg/hr) | Half-life (t ½; hr) |
|---|---|---|
| 5 | >0.04 | 6 |
| 6 | <0.02 | 15 |

TABLE 2-continued

| SEQ ID NO: | Clearance (L/kg/hr) | Half-life (t ½; hr) |
|---|---|---|
| 7 | <0.02 | 17 |
| 8 | >0.04 | 7 |
| 9 | <0.02 | 12 |
| 10 | <0.02 | 21 |

As shown in Table 2, each of SEQ ID NOs:6, 7, 9, and 10 exhibit an increased biological half-life ("t½"). SEQ ID NO:8, which contains a leucine at amino acid position 21, but not at either of amino acid positions 24 or 31, does not exhibit the dramatic increase in half-life exhibited by the peptides of SEQ ID NOs:6, 7, 9, and 10.

For formulating an HIV fusion inhibitor into a pharmaceutically acceptable carrier in producing a pharmaceutical composition, stability in aqueous solution may be an important parameter, particularly if the pharmaceutical composition is to be administered parenterally. It is noted that an HIV fusion inhibitor peptide according to the present invention demonstrates improvement in stability in aqueous solutions at physiological pH. For example, synthetic peptides having an amino acid sequence of SEQ ID NO:2, SEQ ID NO:5, and an HIV fusion inhibitor peptide having an amino acid sequence of SEQ ID NO:9, were each individually tested for solubility by adding the peptide at a concentration of 10 mg/ml to phosphate-buffered saline (PBS), and by measuring (e.g., by HPLC) at different time points over a period of 1 week (168 hours) the amount of peptide remaining in solution at a range of about pH 7.3 to about pH 7.5 at 37° C. A solution containing SEQ ID NO:2 becomes unstable after just several hours (minimal peptide detected in solution). In contrast, 90% or more of the HIV fusion inhibitor peptide having an amino acid sequence of SEQ ID NO:9 remains detectable in solution at a time point of 1 week, whereas less than 80% of a peptide having the amino acid sequence of SEQ ID NO:5 remains detectable in solution at a time point of 1 week.

Example 3

Biological properties of the HIV fusion inhibitor peptides of the present invention have been compared with other recognized, effective antiviral agents, including SEQ ID NO:2 (enfuvirtide). In particular, in vitro resistance comparison studies were performed between the novel SEQ ID NO:9 compound of interest and established antiviral agent SEQ ID NO:2, described in detail as follows:

MT2 cells were infected with virus isolates (IIIB, 030, 060 and 098) and cultured in increasing concentrations of SEQ ID NO:2 (enfuvirtide) or SEQ ID NO:9 to select for resistance. The initial peptide concentration was approximately 2 times the $IC_{50}$ of each peptide against the corresponding wild type isolate. Peptide concentrations were maintained by adding fresh peptide every 1-3 days. Cultures were monitored for cytopathic effect (CPE) using standard techniques and when maximal CPE was achieved, a small aliquot of virus was used for subsequent rounds of infection. Peptide concentrations were increased 2 to 4-fold depending on the length of time in culture when compared to the growth rate of wild type virus. During the course of selection, peptide-free virus stocks were also collected. Peptide-free virus stocks were characterized for gp41 genotypic changes by dideoxy sequencing chemistries and phenotypic susceptibility was determined using a cMAGI infectivity assay.

TABLE 3

Comparison between SEQ ID NO: 2 (enfuvirtide) and SEQ ID NO: 9 in vitro selections

| Starting Virus Isolate | Peptide (SEQ ID NO) | Days in Culture | Starting IC50 (ng/mL) | Ending IC50 (ng/mL) | Fold Change in IC50 | # of Mutations Acquired |
|---|---|---|---|---|---|---|
| IIIB | 2 | 62 | 6 | 163 | 27 | 2 |
| 584.000030 | 2 | 46 | 42 | 798 | 19 | 2 |
| 584.000060 | 2 | 46 | 10 | 68 | 7 | 2 |
| 584.000098 | 2 | 45 | 50 | 45575 | 912 | 1 |
| Geometric Mean | 2 | 49 | 19 | 797 | 42 | 1.7 |
| IIIB | 9 | 168 | 12 | 2768 | 231 | 4 |
| 584.000030 | 9 | 77 | 28 | 113 | 4 | 2 |
| 584.000060 | 9 | 173 | 8 | 208 | 26 | 4 |
| 584.000098 | 9 | 173 | 37 | 521 | 14 | 5 |
| Geometric Mean | 9 | 140 | 18 | 429 | 24 | 3.6 |

The results of comparison between in vitro selections using SEQ ID NO:2 and SEQ ID NO:9 are shown in Table 3. These data show that SEQ ID NO:9 selections were in culture an average of 3 times longer than SEQ ID NO:2 selections, resulting in lower fold changes in IC50 (42-fold for SEQ ID NO:2 compared to 24-fold for SEQ ID NO:9). SEQ ID NO:9 selections required more mutations (geometric mean of 3.6) to achieve these lower fold changes than did SEQ ID NO:2 (geometric mean of 1.7). The longer days in culture, lower fold changes and higher number of mutations required to effect the lower fold changes, all indicate that SEQ ID NO:9 exhibits a higher barrier to development of resistance in vitro compared to SEQ ID NO:2. That is, these results indicate that HIV resistance to SEQ ID NO:9 takes longer to arise than resistance to SEQ ID NO:2. Based on previous studies of HIV resistance development conducted on other peptides, e.g., SEQ ID NO:2 and T1249, one would expect that the in vitro results presented herein should reasonably correlate with results in vivo (see, e.g., Melby et al., 2006, *AIDS Research and Human Retroviruses* 22(5):375-385; Greenberg & Cammack, 2004, *J. Antimicrobial Chemotherapy* 54:333-340; Sista et al., 2004, *AIDS* 18:1787-1794).

Example 4

In general, an HIV fusion inhibitor peptide according to the present invention can be synthesized by each of two methods. A first method is by linear synthesis using standard solid-phase synthesis techniques and using standard Fmoc peptide chemistry or other standard peptide chemistry (using CPGs). A more preferred method for synthesis of an HIV fusion inhibitor peptide according to the present invention is by a fragment condensation approach. Briefly, 2 or more fragments, each fragment containing a respective portion of the complete amino acid sequence of the HIV fusion inhibitor peptide to be produced, is synthesized. In the synthesis of a fragment, if desired, incorporated may be an amino acid having its free amine (e.g., side chain amine) chemically protected by a chemical protecting agent. The fragments are then assembled (covalently coupled together in a manner and order) such that the HIV fusion inhibitor peptide is produced (with the proper amino acid sequence).

With respect to peptide synthesis, the individual peptide fragments themselves, and the HIV fusion inhibitor peptide according to the present invention which is produced from a combination of a group of peptide fragments according to the present invention, may each be made using techniques known to those skilled in the art for synthesizing peptide sequences. For example, in a preferred approach, the peptide fragments may be synthesized in solid phase, and then combined in solution phase, in a process of assembly to produce the resultant HIV fusion inhibitor peptide. In another approach, solution phase synthesis may be used to produce the peptide fragments, which then are combined in solid phase in a process of assembly to produce the HIV fusion inhibitor peptide. In still another approach, each peptide fragment may be synthesized using solid phase synthesis, and then combined in solid phase in a process of assembly to produce the complete amino acid sequence of the HIV fusion inhibitor peptide. In a preferred embodiment, each peptide fragment is produced using solid phase synthesis known to those skilled in the art. In a preferred embodiment, an HIV fusion inhibitor peptide having the amino acid sequence of SEQ ID NO:9 is produced using an assembly process that combines solid phase and solution phase techniques using a group of peptide fragments according to the present invention. For example, a group of peptide fragments comprises between 2 to 4 peptide fragments that are synthesized, and then assembled, to complete the synthesis of an HIV fusion inhibitor peptide according to the present invention. Based on the teachings herein, it is apparent to one skilled in the art that this approach of fragment assembly can be used, and has been used, for some of the HIV fusion inhibitor peptides having an amino acid sequence of any one of SEQ ID NOs:9-16.

To illustrate production of an HIV fusion inhibitor peptide according to the present invention by the fragment condensation approach, peptides fragments, in a group of peptide fragments, were covalently coupled in assembling the peptide fragments in a method of synthesizing an HIV fusion inhibitor peptide having an amino acid sequence of SEQ ID NO:9. The peptide fragments of the invention may include, but are not limited to, those having the amino acid sequences depicted in the following Table 4. Preferred peptide fragment(s) may be used in the present invention to the exclusion of peptide fragment(s) other than the preferred peptide fragment(s). The corresponding amino acids in SEQ ID NO:9 of each peptide fragment are also indicated; thus, it is shown that each peptide fragment is made up of a number of contiguous amino acids of the amino acid sequence of SEQ ID NO:9.

TABLE 4

| SEQ ID NO: | Amino acid sequence | Amino acid positions in SEQ ID NO: 9 |
|---|---|---|
| 17 | TTWEAWDRAIAE | 1-12 |
| 18 | YAARIEALLRALQE | 13-26 |
| 19 | QQEKNEAALRE | 27-37 |
| 20 | QQEKNEAALREL | 27-38 |
| 21 | TTWEAWDRAIA | 1-11 |
| 22 | EYAARIEALLRALQE | 12-26 |
| 23 | TTWEAWDRAI | 1-10 |
| 24 | AEYAARIEALLRALQE | 11-26 |
| 25 | TTWEAWDRA | 1-9 |
| 26 | IAEYAARIEALLRALQE | 10-26 |
| 27 | TTWEAWDR | 1-8 |
| 28 | AIAEYAARIEALLRALQE | 9-26 |
| 29 | TTWEAWDRAIAEYAARIEAL | 1-20 |
| 30 | LRALQEQQEKNEAALRE | 21-37 |
| 31 | LRALQEQQEKNEAALREL | 21-38 |
| 32 | TTWEAWDRAIAEYAARIE | 1-18 |
| 33 | ALLRALQEQQEKNEAALRE | 19-37 |
| 34 | ALLRALQEQQEKNEAALREL | 19-38 |
| 35 | YAARIE ALLRALQEQQEKNEAALREL | 13-38 |
| 36 | EYAARIE ALLRALQEQQEKNEAALREL | 12-38 |
| 37 | AEYAARIE ALLRALQEQQEKNEAALREL | 11-38 |
| 38 | IAEYAARIE ALLRALQEQQEKNEAALREL | 10-38 |
| 39 | AIAEYAARIE ALLRALQEQQEKNEAALREL | 9-38 |
| 40 | TTWEAWDRAIAEYAARIEALLRALQE | 1-26 |

The present invention also encompasses particular groups of peptide fragments which act as intermediates in a method of synthesis of an HIV fusion inhibitor peptide having the amino acid sequence of SEQ ID NO:9. The groups of peptide fragments according to the invention include Groups 1-16, as designated in Table 5 (the numbering of a group is for ease of description only). Preferred group(s) of peptide fragments may be used in the present invention to the exclusion of group(s) of peptide fragments other than the preferred group(s) of peptide fragments.

TABLE 5

| Group Number | Peptide fragments | | Amino acid positions in SEQ ID NO: 9 |
|---|---|---|---|
| 1 | TTWEAWDRAIAE | (SEQ ID NO: 17) | 1-12 |
| | YAARIEALLRALQE | (SEQ ID NO: 18) | 13-26 |
| | QQEKNEAALRE | (SEQ ID NO: 19) | 27-37 |

TABLE 5-continued

| Group Number | Peptide fragments | | Amino acid positions in SEQ ID NO: 9 |
|---|---|---|---|
| 2 | TTWEAWDRAIAE | (SEQ ID NO: 17) | 1-12 |
|   | YAARIEALLRALQE | (SEQ ID NO: 18) | 13-26 |
|   | QQEKNEAALREL | (SEQ ID NO: 20) | 27-38 |
| 3 | TTWEAWDRAIAEYAARIEAL | (SEQ ID NO: 29) | 1-20 |
|   | LRALQEQQEKNEAALRE | (SEQ ID NO: 30) | 21-37 |
| 4 | TTWEAWDRAIAEYAARIEAL | (SEQ ID NO: 29) | 1-20 |
|   | LRALQEQQEKNEAALREL | (SEQ ID NO: 31) | 21-38 |
| 5 | TTWEAWDRAIA | (SEQ ID NO: 21) | 1-11 |
|   | EYAARIEALLRALQE | (SEQ ID NO: 22) | 12-26 |
|   | QQEKNEAALRE | (SEQ ID NO: 19) | 27-37 |
| 6 | TTWEAWDRAI | (SEQ ID NO: 23) | 1-10 |
|   | AEYAARIEALLRALQE | (SEQ ID NO: 24) | 11-26 |
|   | QQEKNEAALRE | (SEQ ID NO: 19) | 27-37 |
| 7 | TTWEAWDRA | (SEQ ID NO: 25) | 1-9 |
|   | IAEYAARIEALLRALQE | (SEQ ID NO: 26) | 10-26 |
|   | QQEKNEAALRE | (SEQ ID NO: 19) | 27-37 |
| 8 | TTWEAWDR | (SEQ ID NO: 27) | 1-8 |
|   | AIAEYAARIEALLRALQE | (SEQ ID NO: 28) | 9-26 |
|   | QQEKNEAALRE | (SEQ ID NO: 19) | 27-37 |
| 9 | TTWEAWDRAIA | (SEQ ID NO: 21) | 1-11 |
|   | EYAARIEALLRALQE | (SEQ ID NO: 22) | 12-26 |
|   | QQEKNEAALREL | (SEQ ID NO: 20) | 27-38 |
| 10 | TTWEAWDRAI | (SEQ ID NO: 23) | 1-10 |
|   | AEYAARIEALLRALQE | (SEQ ID NO: 24) | 11-26 |
|   | QQEKNEAALREL | (SEQ ID NO: 20) | 27-38 |
| 11 | TTWEAWDRA | (SEQ ID NO: 25) | 1-9 |
|   | IAEYAARIEALLRALQE | (SEQ ID NO: 26) | 10-26 |
|   | QQEKNEAALREL | (SEQ ID NO: 20) | 27-38 |
| 12 | TTWEAWDR | (SEQ ID NO: 27) | 1-8 |
|   | AIAEYAARIEALLRALQE | (SEQ ID NO: 28) | 9-26 |
|   | QQEKNEAALREL | (SEQ ID NO: 20) | 27-38 |
| 13 | TTWEAWDRAIAEYAARIE | (SEQ ID NO: 32) | 1-18 |
|   | ALLRALQEQQEKNEAALRE | (SEQ ID NO: 33) | 19-37 |
| 14 | TTWEAWDRAIAEYAARIE | (SEQ ID NO: 32) | 1-18 |
|   | ALLRALQEQQEKNEAALREL | (SEQ ID NO: 34) | 19-38 |
| 15 | TTWEAWDRAIAEYAARIEALLRALQE | (SEQ ID NO: 40) | 1-26 |
|   | QQEKNEAALRE | (SEQ ID NO: 19) | 27-37 |
| 16 | TTWEAWDRAIAEYAARIEALLRALQE | (SEQ ID NO: 40) | 1-26 |
|   | QQEKNEAALREL | (SEQ ID NO: 20) | 27-38 |

Thus, one embodiment of the present invention relates to methods, peptide fragments, and groups of peptide fragments that may be used to synthesize an HIV fusion inhibitor peptide having the amino acid sequence of SEQ ID NO:9. It is also apparent from the description herein that such methods, peptide fragments, and groups of peptide fragments may be used to synthesize an HIV fusion inhibitor peptide having the amino acid sequence of SEQ ID NO:9, wherein the HIV fusion inhibitor peptide contains one or more chemical groups:

B-TTWEAWDRAIAEYAARIEALLRALQEQQEKNEAALREL-Z
|
U wherein one or more of the amino terminal end, carboxyl terminal end, or side chain free reactive functionality (e.g., an epsilon amine of an internal lysine) is modified by a chemical group (B, U, Z; wherein B, U, and Z may be the same chemical group or different chemical groups) which may include, but is not limited to, one or more of: a reactive functionality, a chemical protecting group (CPG), and a linker. Techniques useful for introducing a chemical group at the N-terminus of a peptide fragment, or the C-terminus of a peptide fragment, at a free amine at an internal amino acid, or a combination thereof, are well known in the art. Illustrative examples of protected peptide fragments (peptide fragments having one or more chemical groups), as related to the production of an HIV fusion inhibitor peptide having an amino acid sequence of SEQ ID NO:9, include, but are not limited to, the peptide fragments listed in Table 6.

TABLE 6

| SEQ ID NO: | Amino acid sequence | Amino acid positions in SEQ ID NO: 9 |
|---|---|---|
| 17 | Ac-TTWEAWDRAIAE | 1-12 |
| 18 | CPG-YAARIEALLRALQE | 13-26 |
| 19 | CPG-QQEKNEAALRE | 27-37 |
| 19 | CPG-QQEKNEAALRE<br>↑<br>U | 27-37 |
| 20 | QQEKNEAALREL-NH$_2$ | 27-38 |
| 29 | Ac-TTWEAWDRAIAEYAARIEAL | 1-20 |
| 30 | CPG-LRALQEQQEKNEAALRE | 21-37 |
| 31 | LRALQEQQEKNEAALRE L-NH$_2$ | 21-38 |
| 21 | Ac-TTWEAWDRAIA | 1-11 |
| 22 | CPG-EYAARIEALLRALQE | 12-26 |
| 23 | Ac-TTWEAWDRAI | 1-10 |
| 24 | CPG-AEYAARIEALLRALQE | 11-26 |
| 25 | Ac-TTWEAWDRA | 1-9 |
| 26 | CPG-IAEYAARIEALLRALQE | 10-26 |
| 27 | Ac-TTWEAWDR | 1-8 |
| 28 | CPG-AIAEYAARIEALLRALQE | 9-26 |
| 32 | Ac-TTWEAWDRAIAEYAARIE | 1-18 |
| 33 | CPG-ALLRALQEQQEKNEAALRE | 19-37 |
| 34 | ALLRALQEQQEKNEAALRE L-NH$_2$ | 19-38 |

Ac-acetyl group, NH$_2$-amide group (but can be another chemical group as described in more detail in the "Definitions" section herein); CPG is chemical protecting group (e.g., Fmoc or other N-terminal chemical protecting group, as described in more detail in the "Definitions" section herein); U is as defined above.

Example 5

Figure 3:
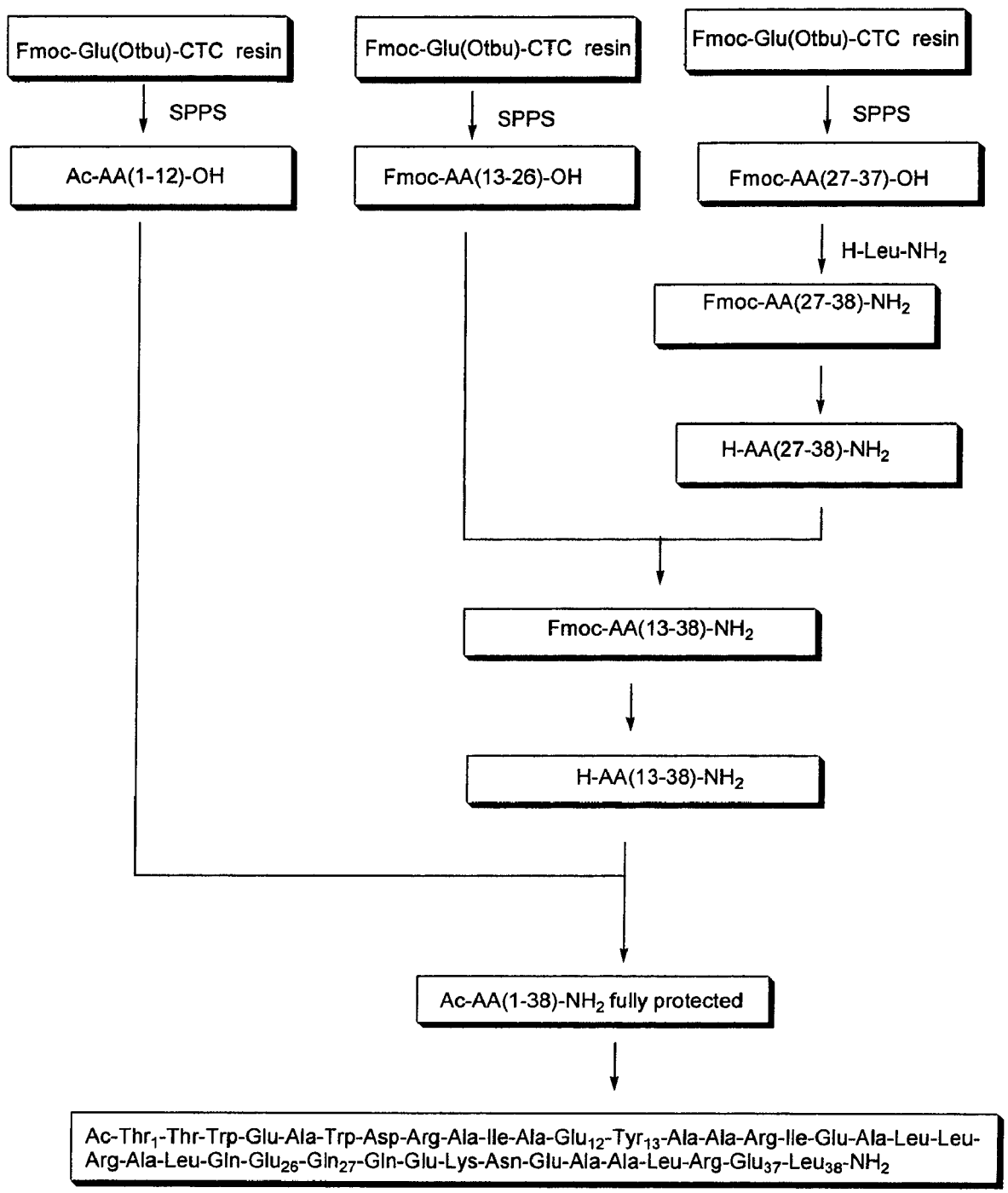
FIG. 3 is a schematic showing synthesis of an HIV fusion inhibitor peptide SEQ ID NO:9, having an amino acid sequence of SEQ ID NO:9, using a fragment condensation approach involving assembly of 3 peptide fragments.

In referring to Table 5 (Group 1 or Group 2) and FIG. 3, illustrated is a method for synthesis of an HIV fusion inhibitor peptide having the amino acid sequence of SEQ ID NO:9 using 3 specific peptide fragments (e.g., SEQ ID NOs:17-19+ Leu; or SEQ ID NOs:17, 18, and 20), and using a fragment condensation approach involving combining the 3 peptide fragments to produce the HIV fusion inhibitor peptide. Each of these peptide fragments demonstrated physical properties and solubility characteristics that make them preferred peptide fragments (relative to a two fragment approach) to be used in a method for synthesis of an HIV fusion inhibitor peptide having the amino acid sequence of SEQ ID NO:9 in high yield and high purity, and further requires only one loaded resin as starting material (in simplifying the method for synthesis). A peptide fragment having the amino acid sequence of SEQ ID NO:17, and comprising the first 12 amino acids of SEQ ID NO:9 (see FIG. 3, "AA(1-12)", was synthesized by standard solid phase synthesis (using a super acid sensitive resin; e.g., 4-hydroxymethyl-3-methoxyphenoxy-butyric acid resin, or 2-chlorotrityl chloride resin-"CTC", FIG. 3), with acetylation of ("Ac", as a chemical group) the N-terminus, while having a hydroxyl group (—OH) at the C-terminus (see, FIG. 3, "Ac-AA(1-12)-OH"). A peptide fragment having the amino acid sequence of SEQ ID NO:18, and comprising amino acids 13-26 of SEQ ID NO:9 (see, FIG. 3, "AA(13-26)"), was synthesized by standard solid phase synthesis with Fmoc at the N-terminus (as a chemical protecting group), and —OH at the C-terminus (see, FIG. 3, "Fmoc-AA(13-26)-OH"). A peptide fragment having the amino acid sequence of SEQ ID NO:19, and comprising amino acids 27-37 of SEQ ID NO:9 (see, FIG. 3, "AA(27-37)"), was synthesized by standard solid phase synthesis with Fmoc at the N-terminus (as a chemical protecting group), and —OH at the C-terminus (see, FIG. 3, "Fmoc-AA(27-37)-OH"). Each peptide fragment was cleaved from the resin used for its solid phase synthesis by cleavage reagents, solvents, and techniques well known to those skilled in the art. Each peptide fragment was then isolated by removing the majority of above mentioned solvents by distillation and precipitating the peptide fragment by the addition of water with or without an alcohol containing-cosolvent. The resulting solid was isolated by filtration, washed, reslurried in water or alcohol/water, refiltered, and dried in a vacuum oven.

As shown in FIG. 3, a peptide fragment was produced by solution phase synthesis, wherein the peptide fragment having the amino acid sequence of SEQ ID NO:19 (see, FIG. 3, "Fmoc-AA(27-37)-OH") was chemically coupled to Leu, amino acid 38 of SEQ ID NO:9, which has been amidated in solution phase to result in a peptide fragment having the amino acid sequence of SEQ ID NO:20 (comprising amino acids 27-38 of SEQ ID NO:9) with amidation of the C-terminus (as a chemical group) (see, FIG. 3, "Fmoc-AA(27-38)-NH$_2$"). In a preferred method of synthesis, amidated peptide fragments of the present invention, including but not limited to peptide fragment H-AA(27-38)-NH$_2$, may be synthesized directly using an amide resin. In summary of this solution phase reaction, the carboxy terminus of isolated peptide fragment Fmoc-AA(27-37)-OH is converted to an active ester of HOBT (1-hydroxybenzotriazole hydrate) 6-Cl HOBt, or HOAT (1-Hydroxy-7-azabenzotriazole) using HBTU (O-benzotriazol-1-yl-N,N,N',N'-tetramethyluronium hexafluorophosphate) or TBTU (O-benzotriazol-1-yl-N,N, N',N'-tetramethyltetrafluoro-borate) and HOBT, 6-Cl HOBT, or HOAT, respectively, in the presence of DIEA (diisopropylethyl amine) and leucine amide (e.g., a combination of coupling reagents and racemization suppressants). The reaction is run in a polar, aprotic solvent such as DMF (dimethyl formamide) or NMP (N-methyl pyrrolidinone) at 0 to 30° C. At the completion of the coupling reaction, piperidine, potassium carbonate, DBU or other bases known to those in the art are added to the reaction with or without an additional cosolvent to effect removal of the terminal Fmoc protecting groups. At the completion of the reaction, alcohol or a water miscible solvent and/or water are added to precipitate the peptide fragment having the amino acid sequence of SEQ ID NO:20 with amidation of the C-terminus (H-AA(27-38)-NH$_2$).

As schematically illustrated in FIG. 3, to produce peptide fragment H-AA(27-38)-NH$_2$ using a peptide fragment Fmoc-AA(27-37)-OH combined with leucine amide (see, FIG. 3, "H-Leu-NH$_2$") in a solution phase process, the peptide fragment Fmoc-AA(27-37)-OH (571 g, 205 mmol, 1 eq), H-Leu-NH$_2$ (32.0 g, 246 mmol, 1.2 eq), and 6-Cl HOBT (41.7 g, 246 mmol, 1.2 eq) were added to DMF (4568 ml, 8 vol), treated with DIEA (53.6 ml, 307.5 mmol, 1.5 eq) and stirred at room temperature until dissolved (about 20 minutes). The solution was cooled and TBTU (79.0 g, 246 mmol, 1.2 eq) was added. The reaction was stirred for at 0° C., then at 25° C. When analysis by HPLC showed the reaction was complete, piperidine (81 ml, 820 mmol, 4 eq) was added to remove the Fmoc protecting group (other bases such as potassium carbonate, DBU, etc., could be used) of the peptide fragment Fmoc-AA (27-38)-NH$_2$. The reaction was stirred at 30° C. until shown to be complete by HPLC. Then the reaction mixture was cooled below 5° C. and pre-cooled water (8 vol, 4568 mL) was slowly added keeping the temperature of the resulting slurry below 10° C. The suspension was stirred for 30 minutes, and then filtered and washed twice with 25% ethanol/water (2284 mL, 4 vol each). Residual piperidine and piperidine dibenzylfulvene was removed by reslurries in ethanol/ water (with or without dilute acid) and/or MTBE/heptane or other similar solvent mixtures. As shown in FIG. 3, the result was a preparation of isolated peptide fragment H-AA(27-38)-$NH_2$.

As illustrated in FIG. 3, a solution phase reaction was then performed in which peptide fragment H-AA(27-38)-$NH_2$ (SEQ ID NO:20) is combined with peptide fragment Fmoc-AA(13-26)-OH (SEQ ID NO:18) and deprotected to yield a peptide fragment H-AA(13-38)-$NH_2$ (SEQ ID NO:35 with chemical groups at each of the N-terminus and C-terminus).

Peptide fragment Fmoc-AA(13-26)-OH (460 g, 167 mmol, 1 eq), peptide fragment H-AA(27-38)-$NH_2$ (460 g, 172 mmol, 1.03 eq), and 6-Cl HOBT (34 g, 200 mmol, 1.2 eq) were added to DMF (6900 ml, 15 vol), treated with DIEA (47 mL, 267 mmol., 1.6 eq), and stirred to dissolve all solids. The resulting solution was cooled to below 5° C. To the reaction was added TBTU (64 g, 200 mmol, 1.2 eq), and the reaction was stirred at 0° C. and then at 25° C. Once analysis by HPLC showed the reaction was complete, piperidine (58 ml, 668 mmol, 4 eq) was added to remove the Fmoc, and the reaction stirred until shown complete by HPLC. The solution was cooled to below 5° C. and water (6900 mL, 15 vol) was slowly added at a rate such that the temperature did not rise above 110° C. After stirring the resulting suspension for 30 minutes, the solids were collected by filtration and washed with water (twice, 2300 mL, 5 vol each), and dried. Residual piperidine and piperidine dibenzylfulvene was removed by reslurries in ethanol/water (with or without dilute acid) and/or MTBE/ heptane or other similar solvent mixtures. The solids were collected by filtration, washed, and dried affording H-AA(13-38)-$NH_2$ (SEQ ID NO:35) as a substantially pure white solid as determined by high performance liquid chromatography (HPLC) analysis for purity.

As illustrated in FIG. 3, peptide fragment H-AA(13-38)-$NH_2$ (SEQ ID NO:35) was then assembled in a solution phase reaction with peptide fragment Ac-(1-12)-OH (SEQ ID NO:17) to yield an HIV fusion inhibitor peptide having the amino acid sequence of SEQ ID NO:9 (see, e.g., FIG. 3, Ac-(1-38)-$NH_2$). Peptide fragment Ac-AA(1-12)-OH (130 g, 58.5 mmol, 1 eq) was milled to a fine powder and mixed with peptide fragment H-AA(13-38)-$NH_2$ (303 g, 58.5 mmol, 1 eq). This mixture was slowly added to a warm solution of 2:1 DCM/DMF (20 vol, 2600 mL) and DIEA (25.5 mL, 146 mmol, 2.5 eq). HOAT (15.9 g, 117 mmol, 2.0 eq) was added and the mixture was stirred to dissolve all solids. The resulting solution was cooled to below 5° C. and TBTU (28.2 g, 87.8 mmol, 1.5 eq) was added. The solution was stirred for 30 minutes at 0° C. and then at 25° C., until HPLC showed the reaction was complete. The solution was warmed to 30-35° C. and additional DCM (13 vol, 1740 mL) followed by $H_2O$ (1820 mL, 14 vol) was added. The mixture was stirred for 5 min and then the layers were allowed to separate. The aqueous layer was removed and replaced with fresh $H_2O$ (1820 mL, 14 vol). The separation was repeated a total of 5 times. The organic layer was distilled to approximately ⅓ its original volume and isopropyl alcohol (IPA; 1820 mL, 14 vol) was added. The distillation was continued to remove the remaining DCM. The resulting slurry was cooled to below 5° C. and $H_2O$ (1820 mL, 14 vol) was slowly added. The solids formed were collected by filtration, washed twice with $H_2O$ (520 mL, 4 vol each) and dried affording a preparation of isolated HIV fusion inhibitor peptide Ac-AA(1-38)-$NH_2$ (SEQ ID NO:9), as determined by HPLC analysis for purity.

As shown in FIG. 3, the side chain chemical protecting groups of HIV fusion inhibitor peptide Ac-AA(1-38)-$NH_2$ may be removed by acidolysis or any other method known to those skilled in the art for deprotecting a peptide by removing side chain chemical protecting groups. In this example, HIV fusion inhibitor peptide Ac-AA(1-38)-$NH_2$ (60 g, 8.1 mmol) was treated with TFA (trifluoracetic acid):DTT (dithiothreitol):water (90:10:5; 570 ml) and stirred at room temperature for 6 hours. The solution was cooled to below 10° C., and pre-cooled MTBE (25 vol, 1500 ml) was slowly added at a rate such that the temperature remained below 10° C. The resulting solids were collected by filtration, washed with MTBE, and dried. The resulting powder was then slurried in acetonitrile (ACN; 10 vol, 600 mL) and the pH was adjusted to between 4 and 5 with DIEA and acetic acid to decarboxylate the peptide. Once this was complete by HPLC, the solids were collected by filtration, washed with ACN, and dried to yield a preparation of deprotected and decarboxylated peptide, which was then purified by HPLC or other suitable chromatographic techniques to yield a preparation of isolated HIV fusion inhibitor peptide having an amino acid sequence of SEQ ID NO:9.

Example 6

Figure 4:
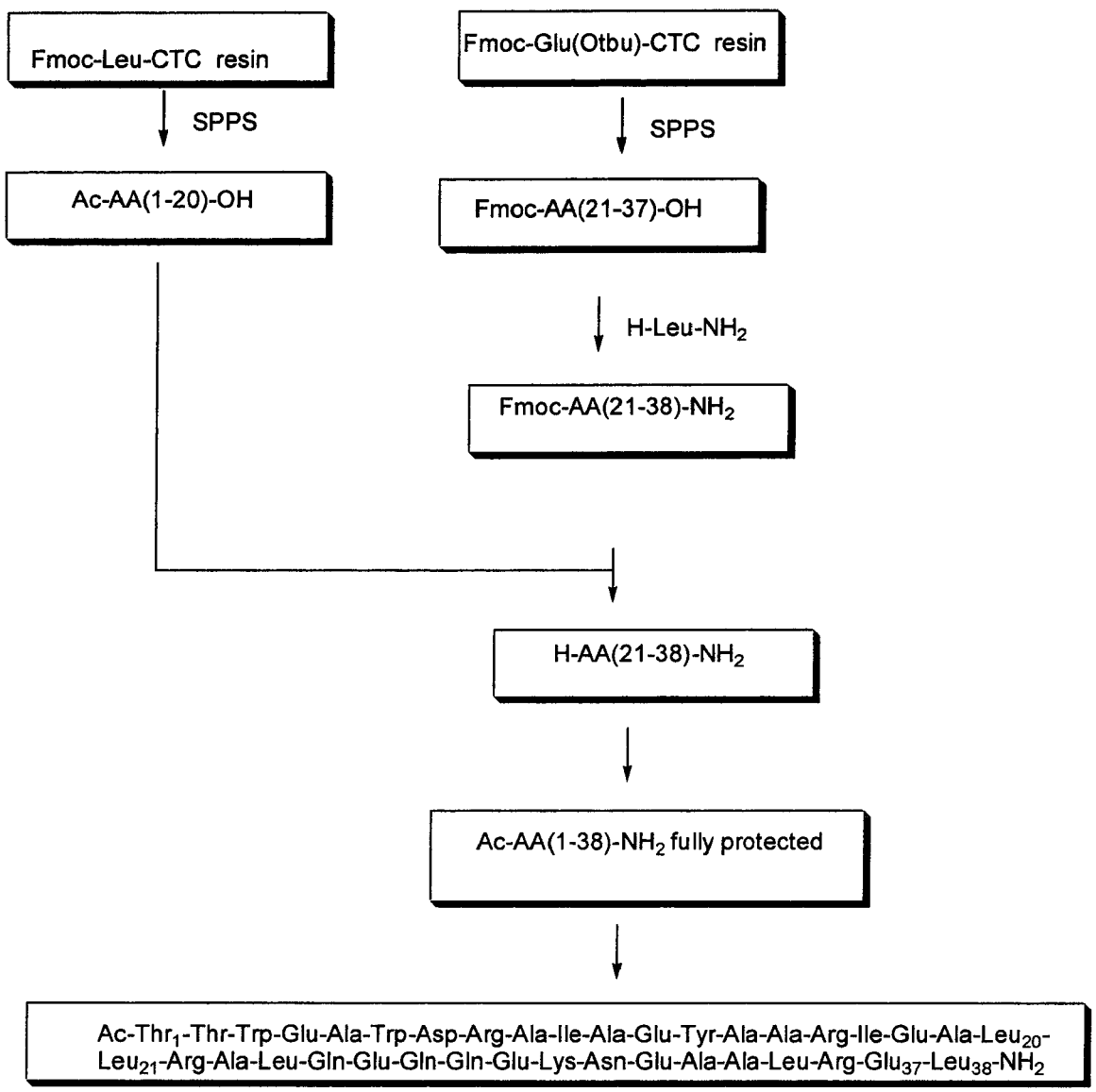
FIG. 4 is a schematic showing synthesis of an HIV fusion inhibitor peptide SEQ ID NO:9, having an amino acid sequence of SEQ ID NO:9, using a fragment condensation approach involving assembly of 2 peptide fragments.

In referring to Table 5 (Group 3 and Group 4) and FIG. 4, illustrated is a method for synthesis of a HIV fusion inhibitor peptide having the amino acid sequence of SEQ ID NO:9 using 2 specific peptide fragments (e.g., SEQ ID NOs:29 & 30+Leu; or SEQ ID NOs:29 & 31), and using a fragment assembly approach involving combining 2 peptide fragments by chemically coupling ("assembling") them to produce HIV fusion inhibitor peptide having an amino acid sequence of SEQ ID NO:9. Each of these peptide fragments demonstrated physical properties and solubility characteristics that make them preferable in a method for synthesis, using 2 peptide fragments, of an HIV fusion inhibitor peptide having the amino acid sequence of SEQ ID NO:9 in high yield and purity. In selecting peptide fragments to be used in a two fragment assembly approach, it was discovered that having leucine and/or glutamic acid residues at the point of juncture between the two fragments being assembled together (e.g., the C-terminal amino acid of a peptide fragment having the amino acid sequence of SEQ ID NO:29, and the N-terminal amino acid of a peptide fragment having the amino acid sequence of SEQ ID NO:31) favored assembly in the high yield and the degree of purity obtained.

A peptide fragment having the amino acid sequence of SEQ ID NO:29, and comprising the first 20 amino acids of SEQ ID NO:9 ("AA(1-20)"), was synthesized by standard solid phase synthesis, with acetylation of ("Ac", as a chemical group) the N-terminus, while having a hydroxyl group (—OH) at the C-terminus (see, Table 6; also referred to herein as "Ac-AA(1-20)-OH"). A peptide fragment having the amino acid sequence of SEQ ID NO:30, and comprising amino acids 21-37 of SEQ ID NO:9 ("AA(21-37)"), was synthesized by standard solid phase synthesis with Fmoc at the N-terminus (as a chemical protecting group), and —OH at the C-terminus (see, Table 6; also referred to herein as "Fmoc-AA(21-37)-OH").

As shown in Table 5, Groups 3 and 4, and FIG. 4, a peptide fragment was produced by solution phase synthesis, when the peptide fragment Fmoc-AA(21-37)-OH was chemically coupled to Leu, amino acid 38 of SEQ ID NO:9 which had been amidated, in solution phase to result in a peptide fragment having the amino acid sequence of SEQ ID NO:31 (comprising amino acids 21-38 of SEQ ID NO:9) with amidation of the C-terminus (as a chemical group) ("Fmoc-AA (21-38)-$NH_2$"). To produce peptide fragment Fmoc-AA(21-38)-$NH_2$ using a peptide fragment Fmoc-AA(21-37)-OH combined with leucine ("H-Leu NH₂") in a solution phase process, the peptide fragment Fmoc-AA(21-37)-OH (30 g, 7.43 mmol, 1.0 eq), H-Leu-NH₂*HCl (1.36 g, 8.16 mmol, 1.2 eq), and HOAT (1.52 g, 11.2 mmol, 1.5 eq) were dissolved in DMF (450 ml, 15 vol), treated with DIEA (6.5 ml, 37.3 mmol, 5 eq), and stirred at room temperature until dissolved (about 30 minutes). The solution was cooled to 0±5° C., and TBTU (2.86 g, 8.91 mmol, 1.2 eq) was added, stirred for 5 minutes at 0±5° C., and then allowed to react at 25±5° C. for 2 hours or until the reaction was shown complete by HPLC.

The Fmoc chemical protecting group of the peptide fragment Fmoc-AA(21-38)-NH₂ was then removed prior to isolation of the fragment H-AA(21-38)-NH₂. Piperidine (7.3 mL. 73.8 mmol, 10 eq) was added and the solution was stirred for 1 hour at 25±5° C. or until analysis by HPLC showed that substantially all the Fmoc was removed from the peptide fragment. The reactor was cooled, and water (1000 ml, 30 vol) was added, and the free-flowing slurry was stirred 30 minutes at less than 10° C., and then isolated by filtration. The collected solid was washed with 1:1 EtOH/water and dried in a vacuum oven at 35±5° C. The peptide fragment is then reslurried in 1:1 EtOH/water (450 mL, 15 vol) for 3 hours. The solids were collected and dried. Then the peptide fragment was slurried in 3:1 hexanes:MTBE (450 mL, 15 vol) overnight, and then isolated by filtration and redried. The MTBE reslurry may be repeated if necessary to remove additional piperidine. The result is a preparation of isolated peptide fragment H-AA(21-38)-NH₂ (see FIG. 4).

A solution phase reaction was then performed in which peptide fragment H-AA(21-38)-NH₂ (SEQ ID NO:31) was combined with peptide fragment Ac-AA(1-20)-OH (SEQ ID NO:29) to yield an HIV fusion inhibitor peptide having the amino acid sequence of SEQ ID NO:9 (see, FIG. 4, Ac-(1-38)-NH₂). Peptide fragment H-AA(21-38)-NH₂ (3.40 g, 0.86 mmol, 1 eq), peptide fragment Ac-AA(1-20)-OH (3.00 g, 0.86 mmol, 1.0 eq), and HOAT (0.177 g, 1.3 mmol, 1.5 eq) and DIEA (0.599 ml, 3.44 mmol, 4 eq) were dissolved in DMAc (dimethyl acetamide; 100 ml, 33 vol), cooled to 0±5° C. Added to the reaction was TBTU (0.331 g, 1.03 mmol, 1.2 eq). The reaction was stirred for 5 minutes at 0±5° C. and at 25±5° C. for 3 hours or until the reaction was shown to be complete by HPLC. The reactor was cooled, and water (200 ml, 66 vol) was slowly added. A slurry was formed and stirred at less than 10° C. for at least 30 minutes. The solid was isolated by filtration and washed with additional water. The collected solid was dried in a vacuum oven at 35±5° C. The result was a preparation of fully protected, isolated HIV fusion inhibitor peptide Ac-AA(1-38)-NH₂ (SEQ ID NO:9), as determined by HPLC analysis for purity. The HIV fusion inhibitor peptide was then deprotected (by removing the side chain chemical protecting groups) and decarboxylated (at the tryptophan residues) by using the methods described herein in Example 5, or any other method known to those skilled in the art, for deprotection and decarboxylation, and then purified (e.g., by HPLC). The result was a preparation (deprotected and decarboxylated) of HIV fusion inhibitor peptide having an amino acid sequence of SEQ ID NO:9 (in this illustration, acetylated at the N-terminus, and amidated at the C-terminus).

Using similar techniques and conditions, additional fragment assembly approaches, involving 2 fragment assembly or 3 fragment assembly, have been used to produce an HIV fusion inhibitor peptide having an amino acid sequence of SEQ ID NO:9 (see, for example, Tables 4 and 5). It is understood from the descriptions herein that preferred peptide fragments, used to produce an HIV fusion inhibitor peptide having an amino acid sequence of SEQ ID NO:9 by the method of the present invention, may be used to the exclusion of peptide fragments other than the preferred peptide fragments. Likewise, a preferred group of peptide fragments, used to produce an HIV fusion inhibitor peptide having an amino acid sequence of SEQ ID NO:9 by the method of the present invention, may be used to the exclusion of groups of peptide fragments other than the preferred group of peptide fragments.

Example 7

Another embodiment of the present invention relates to methods, peptide fragments, and groups of peptide fragments that may be used to synthesize an HIV fusion inhibitor peptide having the amino acid sequence of SEQ ID NO:10. It is also apparent from the description herein that such methods, peptide fragments, and groups of peptide fragments may be used to synthesize an HIV fusion inhibitor peptide having the amino acid sequence of SEQ ID NO:10, wherein the HIV fusion inhibitor peptide contains one or more chemical groups:

B-TTWEAWDRAIAEYAARIEALLRAAQEQQEKLEAALREL-Z
                                      |
                                      U wherein either or both of the amino terminal end or carboxyl terminal end is modified by a chemical group (B, U, Z; wherein B, U, and Z may be the same chemical group or different chemical groups) which may include, but is not limited to, one or more of: a reactive functionality, a chemical protecting group (CPG), and a linker. Illustrative examples of peptide fragments, groups of peptide fragments, and protected peptide fragments (peptide fragments having one or more chemical groups), as related to the production of an HIV fusion inhibitor peptide having an amino acid sequence of SEQ ID NO:10, include, but are not limited to, those listed in Tables 7, 8, & 9, respectively.

TABLE 7

| SEQ ID NO: | Amino acid sequence | Amino acid positions in SEQ ID NO: 10 |
|---|---|---|
| 17 | TTWEAWDRAIAE | 1-12 |
| 41 | YAARIEALLRAAQE | 13-26 |
| 42 | QQEKLEAALRE | 27-37 |
| 43 | QQEKLEAALREL | 27-38 |
| 44 | EYAARIEALLRAAQE | 12-26 |
| 23 | TTWEAWDRAI | 1-10 |
| 45 | AEYAARIEALLRAAQE | 11-26 |
| 25 | TTWEAWDRA | 1-9 |
| 46 | IAEYAARIEALLRAAQE | 10-26 |
| 27 | TTWEAWDR | 1-8 |
| 47 | AIAEYAARIEALLRAAQE | 9-26 |
| 29 | TTWEAWDRAIAEYAARIEAL | 1-20 |

TABLE 7-continued

| SEQ ID NO: | Amino acid sequence | Amino acid positions in SEQ ID NO: 10 |
|---|---|---|
| 48 | LRAAQEQQEKLEAALRE | 21-37 |
| 49 | LRAAQEQQEKLEAALREL | 21-38 |
| 32 | TTWEAWDRAIAEYAARIE | 1-18 |
| 50 | ALLRAAQEQQEKLEAALRE | 19-37 |
| 51 | ALLRAAQEQQEKLEAALREL | 19-38 |
| 52 | YAARIEALLRAAQEQQEKLEAALREL | 13-38 |
| 53 | EYAARIEALLRAAQEQQEKLEAALREL | 12-38 |
| 54 | AEYAARIEALLRAAQEQQEKLEAALREL | 11-38 |
| 55 | IAEYAARIEALLRAAQEQQEKLEAALREL | 10-38 |
| 56 | AIAEYAARIEALLRAAQEQQEKLEAALREL | 9-38 |

The present invention also encompasses particular groups of peptide fragments which act as intermediates in a method of synthesis of an HIV fusion inhibitor peptide having the amino acid sequence of SEQ ID NO:10. The groups of peptide fragments according to the invention include Groups 1-14, as designated in Table 8 (the numbering of a group is for ease of description only). Preferred group(s) of peptide fragments may be used in the present invention to the exclusion of group(s) of peptide fragments other than the preferred group(s) of peptide fragments.

TABLE 8

| Group Number | Peptide fragments | | Amino acid positions in SEQ ID NO: 10 |
|---|---|---|---|
| 1 | TTWEAWDRAIAE | (SEQ ID NO: 17) | 1-12 |
| | YAARIEALLRAAQE | (SEQ ID NO: 41) | 13-26 |
| | QQEKLEAALRE | (SEQ ID NO: 42) | 27-37 |
| 2 | TTWEAWDRAIAE | (SEQ ID NO: 17) | 1-12 |
| | YAARIEALLRAAQE | (SEQ ID NO: 41) | 13-26 |
| | QQEKLEAALREL | (SEQ ID NO: 43) | 27-38 |
| 3 | TTWEAWDRAIAEYAARIEAL | (SEQ ID NO: 29) | 1-20 |
| | LRAAQEQQEKLEAALRE | (SEQ ID NO: 48) | 21-37 |
| 4 | TTWEAWDRAIAEYAARIEAL | (SEQ ID NO: 29) | 1-20 |
| | LRAAQEQQEKLEAALREL | (SEQ ID NO: 49) | 21-38 |
| 5 | TTWEAWDRAIA | (SEQ ID NO: 21) | 1-11 |
| | EYAARIEALLRAAQE | (SEQ ID NO: 44) | 12-26 |
| | QQEKLEAALRE | (SEQ ID NO: 42) | 27-37 |
| 6 | TTWEAWDRAI | (SEQ ID NO: 23) | 1-10 |
| | AEYAARIEALLRAAQE | (SEQ ID NO: 45) | 11-26 |
| | QQEKLEAALRE | (SEQ ID NO: 42) | 27-37 |
| 7 | TTWEAWDRA | (SEQ ID NO: 25) | 1-9 |
| | IAEYAARIEALLRAAQE | (SEQ ID NO: 46) | 10-26 |
| | QQEKLEAALRE | (SEQ ID NO: 42) | 27-37 |
| 8 | TTWEAWDR | (SEQ ID NO: 27) | 1-8 |
| | AIAEYAARIEALLRAAQE | (SEQ ID NO: 47) | 9-26 |
| | QQEKLEAALRE | (SEQ ID NO: 43) | 27-37 |
| 9 | TTWEAWDRAIA | (SEQ ID NO: 21) | 1-11 |
| | EYAARIEALLRAAQE | (SEQ ID NO: 44) | 12-26 |
| | QQEKLEAALREL | (SEQ ID NO: 43) | 27-38 |
| 10 | TTWEAWDRAI | (SEQ ID NO: 23) | 1-10 |
| | AEYAARIEALLRAAQE | (SEQ ID NO: 45) | 11-26 |
| | QQEKLEAALREL | (SEQ ID NO: 43) | 27-38 |
| 11 | TTWEAWDRA | (SEQ ID NO: 25) | 1-9 |
| | IAEYAARIEALLRAAQE | (SEQ ID NO: 46) | 10-26 |
| | QQEKLEAALREL | (SEQ ID NO: 43) | 27-38 |
| 12 | TTWEAWDR | (SEQ ID NO: 27) | 1-8 |
| | AIAEYAARIEALLRAAQE | (SEQ ID NO: 47) | 9-26 |
| | QQEKLEAALREL | (SEQ ID NO: 43) | 27-38 |
| 13 | TTWEAWDRAIAEYAARIE | (SEQ ID NO: 32) | 1-18 |
| | ALLRAAQEQQEKLEAALRE | (SEQ ID NO: 50) | 19-37 |

TABLE 8-continued

| Group Number | Peptide fragments | | Amino acid positions in SEQ ID NO: 10 |
|---|---|---|---|
| 14 | TTWEAWDRAIAEYAARIE | (SEQ ID NO: 32) | 1-18 |
|  | ALLRAAQEQQEKLEAALREL | (SEQ ID NO: 51) | 19-38 |

TABLE 9

| SEQ ID NO: | Amino acid sequence | Amino acid positions in SEQ ID NO: 10 |
|---|---|---|
| 17 | Ac-TTWEAWDRAIAE | 1-12 |
| 41 | CPG-YAARIEALLRAAQE | 13-26 |
| 42 | CPG-QQEKLEAALRE | 27-37 |
| 42 | CPG-QQEKLEAALRE ↑ IvDde | 27-37 |
| 43 | QQEKLEAALREL-NH$_2$ | 27-38 |
| 29 | Ac-TTWEAWDRAIAEYAARIEAL | 1-20 |
| 48 | CPG-LRAAQEQQEKLEAALRE | 21-37 |
| 49 | LRAAQEQQEKLEAALRE L-NH$_2$ | 21-38 |
| 21 | Ac-TTWEAWDRAIA | 1-11 |
| 44 | CPG-EYAARIEALLRAAQE | 12-26 |
| 23 | Ac-TTWEAWDRAI | 1-10 |
| 45 | CPG-AEYAARIEALLRAAQE | 11-26 |
| 25 | Ac-TTWEAWDRA | 1-9 |
| 46 | CPG-IAEYAARIEALLRALQE | 10-26 |
| 27 | Ac-TTWEAWDR | 1-8 |
| 47 | CPG-AIAEYAARIEALLRAAQE | 9-26 |
| 32 | Ac-TTWEAWDRAIAEYAARIE | 1-18 |
| 50 | CPG-ALLRAAQEQQEKLEAALRE | 19-37 |
| 51 | ALLRAAQEQQEKLEAALRE L-NH$_2$ | 19-38 |

In referring to Table 8 (Group 3 and Group 4), illustrated is a method for synthesis of an HIV fusion inhibitor peptide having the amino acid sequence of SEQ ID NO:10 using 2 specific peptide fragments (e.g., SEQ ID NOs:29 & 48+Leu; or SEQ ID NOs:29 & 49), and using a fragment assembly approach involving combining 2 peptide fragments by chemically coupling ("assembling") them to produce an HIV fusion inhibitor peptide having an amino acid sequence of SEQ ID NO:10. To produce peptide fragment having an amino acid sequence of SEQ ID NO:49 ("Fmoc-AA(21-38)-NH$_2$"), using a peptide fragment having an amino acid sequence of SEQ ID NO:48 ("Fmoc-AA(21-37)-OH") combined with leucine ("H-Leu NH$_2$") in a solution phase process, the peptide fragment Fmoc-AA(21-37)-OH (30.01 g, 7.98 mmol, 1.0 eq), H-Leu-NH$_2$*HCl (1.48 g, 8.78 mmol, 1.1 eq), and HOAT (1.63 g, 11.97 mmol, 1.5 eq) were dissolved in DMF (450 ml, 15 vol), treated with DIEA (7.0 ml, 39.91, mmol, 5 eq) and stirred at room temperature until dissolved (about 30 minutes), The solution was cooled to 0±5° C., and TBTU (3.09 g, 9.58 mmol, 1.2 eq) was added, stirred for 5 minutes at 0±5° C., and then allowed to react at 25±5° C. for 2 hours or until the reaction was shown complete by HPLC.

The Fmoc chemical protecting group of the peptide fragment Fmoc-AA(21-38)-NH$_2$ was then removed prior to isolation of the fragment H-AA(21-38)-NH$_2$. Piperidine (8.0 mL, 79.8 mmol, 10 eq) was added and the solution was stirred for 1.5 hours at 25±5° C. or until analysis by HPLC showed that substantially all the Fmoc was removed from the peptide fragment. The reactor was cooled, and water (1000 ml, 30 vol) was added, and the free-flowing slurry was stirred 30 minutes at less than 10° C., and then isolated by filtration. The collected solid was washed with 1:3 EtOH/water and dried in a vacuum oven at 35±5° C. The peptide fragment is then reslurried in 1:3 EtOH/water (400 mL, 13 vol) for 3 hours. The solids were collected and dried, and then the peptide fragment was slurried in 3:1 hexanes:MTBE (400 mL, 13 vol) overnight, isolated by filtration, and redried. The MTBE reslurry may be repeated if necessary to remove additional piperidine. The result is a preparation of isolated peptide fragment H-AA(21-38)-NH$_2$ (see Table 9, SEQ ID NO:49).

A solution phase reaction was then performed in which peptide fragment H-AA(21-38)-NH$_2$ (SEQ ID NO:49) is combined with peptide fragment Ac-AA(1-20)-OH (SEQ ID NO:29, Table 9) to yield an HIV fusion inhibitor peptide having the amino acid sequence of SEQ ID NO:10 (see, e.g., Ac-(1-38)-NH$_2$). Peptide fragment H-AA(21-38)-NH$_2$ (3.14 g, 0.86 mmol, 1 eq), peptide fragment Ac-AA(1-20)-OH (3.00 g, 0.86 mmol, 1.0 eq), and HOAT (0.18 g, 1.3 mmol, 1.5 eq) and DIEA (0.599 ml, 3.44 mmol, 4 eq) were dissolved in DMAc (100 ml, 33 vol), cooled to 0±5° C. Added to the reaction was TBTU (0.331 g, 1.03 mmol, 1.2 eq). The reaction was stirred for 5 minutes at 0±5° C. and at 25±5° C. for 3 hours or until the reaction was shown to be complete by HPLC. The reactor was cooled, and water (250 ml, 83 vol) was slowly added. A slurry was formed and stirred at less than 10° C. for at least 30 minutes. The solid was isolated by filtration and washed with additional water. The collected solid dried in a vacuum oven at 35±5° C. The result was a preparation of fully protected, isolated HIV fusion inhibitor peptide Ac-AA(1-38)-NH$_2$ (SEQ ID NO:10), as determined by HPLC analysis for purity. The HIV fusion inhibitor peptide Ac-AA(1-38)-NH$_2$ was then deprotected (by removing the side chain chemical protecting groups) and decarboxylated (at the tryptophan residues) by using the methods described herein in Example 4, or any other method known to those skilled in the art, for deprotection and decarboxylation. Following purification, the result was a preparation (deprotected and decarboxylated) of isolated HIV fusion inhibitor peptide having an amino acid sequence of SEQ ID NO:10 (acetylated at the N-terminus and amidated at the C-terminus), as determined by HPLC.

Using similar techniques and conditions, additional fragment assembly approaches, involving 2 fragment assembly or 3 fragment assembly, may be used to produce the HIV fusion inhibitor having an amino acid sequence of SEQ ID NO:10 (see, for example, Tables 8 and 9). It is understood from the descriptions herein that preferred peptide fragments, used to produce an HIV fusion inhibitor peptide having an amino acid sequence of SEQ ID NO:10 by the method of the present invention, may be used to the exclusion of peptide fragments other than the preferred peptide fragments. Likewise, a preferred group of peptide fragments, used to produce an HIV fusion inhibitor peptide having an amino acid sequence of SEQ ID NO:10 by the method of the present invention, may be used to the exclusion of groups of peptide fragments other than the preferred group of peptide fragments.

Example 8

The present invention provides for methods for administering an HIV fusion inhibitor peptide according to the present invention, itself or as an active drug substance in a pharmaceutical composition according to the present invention, in treatment of, therapy for, or as part of a therapeutic regimen for, HIV infection and/or AIDS. Antiviral activity of an HIV fusion inhibitor peptide can be utilized in a method for inhibiting transmission of HIV to a target cell, comprising adding to the virus and cell an amount of HIV fusion inhibitor peptide according to the present invention effective to inhibit infection of the cell by HIV, and more preferably, to inhibit HIV-mediated fusion between the virus and the target cell. This method may be used to treat HIV-infected individuals (therapeutically) or to treat individuals newly exposed to or at high risk of exposure (e.g., through drug usage or high risk sexual behavior) to HIV (prophylactically). Thus, for example, in the case of an HIV-1 infected individual, an effective amount of HIV fusion inhibitor peptide would be a dose sufficient (by itself and/or in conjunction with a regimen of doses) to reduce HIV viral load in the individual being treated. As known to those skilled in the art, there are several standard methods for measuring HIV viral load which include, but are not limited to, by quantitative cultures of peripheral blood mononuclear cells and by plasma HIV RNA measurements. The HIV fusion inhibitor peptides of the invention can be administered in a single administration, intermittently, periodically, or continuously, as can be determined by a medical practitioner, such as by monitoring viral load. Depending on the formulation containing HIV fusion inhibitor peptide, and such factors as whether or not the formulation is further comprising a pharmaceutically acceptable carrier and/or macromolecular carrier, the HIV fusion inhibitor peptide according to the present invention may be administered with a periodicity ranging from days to weeks or possibly longer. Further, an HIV fusion inhibitor peptide according to the present invention may be used, in antiviral therapy, when used in combination or in a therapeutic regimen (e.g., when used simultaneously, or in a cycling on with one drug and cycling off with another) with other antiviral drugs or prophylactic agents used for treatment of HIV.

One commonly used treatment involving a combination of antiviral agents is known as HAART (Highly Active Anti-Retroviral Therapy). HAART typically combines three or more drugs with antiviral activity against HIV, and typically involves more than one class of drug (a "class" referring to the mechanism of action, or viral protein or process targeted by the drug). Thus, a method of treatment, an HIV fusion inhibitor peptide, and a pharmaceutical composition, according to the present invention, may be administered alone (e.g., as monotherapy) or may be administered in a treatment regimen, or co-administered, involving a combination of additional therapeutic agents for the treatment of HIV infection and/or AIDS, as described in more detail herein.

For example, in one preferred embodiment, one or more therapeutic agents may be combined in treatment with an HIV fusion inhibitor peptide (by itself, or in a pharmaceutical composition) according to the present invention. Typically, the combination comprises two or more antiviral agents to increase the efficacy of the treatment by, for example, reducing the ability of the virus to become resistant to the antiviral agents used in the treatment (as compared to monotherapy). Such combinations may be prepared from effective amounts of antiviral agents (useful in treating of HIV infection) currently approved or approved in the future, which include, but are not limited to, one or more additional therapeutic agents selected from the following: reverse transcriptase inhibitor, including, but not limited to, abacavir, AZT (zidovudine), ddC (zalcitabine), nevirapine, ddI (didanosine), FTC (emtricitabine), (+) and (−) FTC, reverset, 3TC (lamivudine), GS 840, GW-1592, GW-8248, GW-5634, HBY097, delaviridine, efavirenz, d4T (stavudine), FLT, TMC125, adefovir, tenofovir, and alovudine; protease inhibitor, including but not limited to, amprenivir, CGP-73547, CGP-61755, DMP-450, indinavir, nelfinavir, PNU-140690, ritonavir, saquinavir, telinavir, tipranovir, atazanavir, lopinavir; viral entry inhibitor, including but not limited to, fusion inhibitor (enfuvirtide, T1249, other fusion inhibitor peptides, and small molecules), chemokine receptor antagonist (e.g., CCR5 antagonist, such as ONO-4128, GW-873140, AMD-887, CMPD-167, maraviroc (UK-427857); CXCR4 antagonist, such as AMD-070), an agent which affects viral binding interactions (e.g., affects gp120 and CD4 receptor interactions, such as BMS806, BMS-488043; and/or PRO 542, PRO 140; anti-CD4 antibody; or lipid and/or cholesterol interactions, such as procaine hydrochloride (SP-01 and SP-01A)); integrase inhibitor, including but not limited to, L-870, and 810; RNAseH inhibitor; inhibitor of rev or REV; inhibitor of vif (e.g., vif-derived proline-enriched peptide, HIV-1 protease N-terminal-derived peptide); viral processing inhibitor, including but not limited to betulin, and dihydrobetulin derivatives (e.g., PA-457); and immunomodulator, including but not limited to, AS-101, granulocyte macrophage colony stimulating factor, IL-2, valproic acid, and thymopentin. As appreciated by one skilled in the art of treatment of HIV infection and/or AIDS, a combination drug treatment may comprise two or more therapeutic agents having the same mechanism of action (viral protein or process as a target), or may comprise two or more therapeutic agents having a different mechanism of action.

Effective dosages of these illustrative additional therapeutic agents, which may be used in combinations with an HIV fusion inhibitor peptide, or pharmaceutical composition, according to the present invention, are known in the art. Such combinations may include a number of antiviral agents or therapeutic agents that can be administered by one or more routes, sequentially or simultaneously, depending on the route of administration and desired pharmacological effect, as is apparent to one skilled in the art. Effective dosages of an HIV fusion inhibitor peptide or pharmaceutical composition according to the present invention to be administered may be determined through procedures well known to those in the art; e.g., by determining potency, biological half-life, bioavailability, and toxicity. In a preferred embodiment, an effective amount of an HIV fusion inhibitor peptide according to the present invention and its dosage range are determined by one skilled in the art using data from routine in vitro and in vivo studies well know to those skilled in the art. For example, in vitro infectivity assays of antiviral activity, such as described herein, enables one skilled in the art to determine the mean inhibitory concentration (IC) of the compound, as the sole active ingredient or in combination with other active ingredients, necessary to inhibit a predetermined range of viral infectivity (e.g., 50% inhibition, $IC_{50}$; or 90% inhibition, $IC_{90}$) or viral replication. Appropriate doses can then be selected by one skilled in the art using pharmacokinetic data from one or more standard models, so that a minimum plasma concentration (C[min]) of the active ingredient is obtained which is equal to or exceeds a predetermined value for inhibition of viral infectivity or viral replication. While dosage ranges typically depend on the route of administration chosen and the formulation of the dosage, when administered, such as routes of administration including but not limited to, subcutaneously, parenterally, intradermal or orally, an exemplary dosage range of a compound according to the present invention, as an active ingredient, may be from about 1 mg/kg body weight to about 100 mg/kg body weight; and more preferably no less than 1 mg/kg body weight to no more than 10 mg/kg body weight.

An HIV fusion inhibitor peptide of the present invention may be administered to an individual by any means that enables the active agent to reach the target cells (cells that can be infected by HIV). Thus, the HIV fusion inhibitor peptide of this invention may be administered by any suitable technique, including oral, parenteral (e.g., intramuscular, intraperitoneal, intravenous, or subcutaneous injection or infusion, intradermal, or implant), nasal, pulmonary, vaginal, rectal, sublingual, or topical routes of administration, and can be formulated in dosage forms appropriate for each route of administration. The specific route of administration will depend, e.g., on the medical history of the individual, including any perceived or anticipated side effects from such administration, and the formulation of HIV fusion inhibitor peptide being administered (e.g., the nature of a pharmaceutical carrier and/or macromolecular carrier). Most preferably, administration is by injection (using, e.g., intravenous or subcutaneous means), but could also be by continuous infusion (using, e.g., slow-release devices or minipumps such as osmotic pumps, and the like). In a preferred embodiment, an HIV fusion inhibitor peptide according to the present invention may further comprise a pharmaceutically acceptable carrier; and may further depend on the formulation desired, site of delivery, the method of administration, the scheduling of administration, and other factors known to medical practitioners.

Thus, in accordance with the present invention, there is provided a method for inhibition of transmission of HIV to a cell, comprising administering an HIV fusion inhibitor peptide, or pharmaceutical composition containing HIV fusion inhibitor peptide, according to the present invention in an effective amount to inhibit infection of the cell by HIV. The method may further include administering HIV fusion inhibitor peptide or pharmaceutical composition according to the present invention in combination with other therapeutic agents used to treat HIV infection and/or AIDS to an individual by administering to the individual the combination (simultaneously or sequentially, or a part of a therapeutic regimen) of therapeutic agents which includes an effective amount of the HIV fusion inhibitor peptide or pharmaceutical composition according to the present invention. Also provided is a method for inhibiting HIV entry comprising administering to an individual in need of treatment an HIV fusion inhibitor peptide or pharmaceutical composition according to the present invention in an effective amount to inhibit viral entry of a target cell. The method may further include administering an HIV fusion inhibitor peptide or pharmaceutical composition according to the present invention in combination with one or more additional inhibitors of viral entry useful in treating HIV infection in an effective amount.

The foregoing description of the specific embodiments of the present invention have been described in detail for purposes of illustration. In view of the descriptions and illustrations, others skilled in the art can, by applying current knowledge, readily modify and/or adapt the present invention for various applications without departing from the basic concept; and thus, such modifications and/or adaptations are intended to be within the meaning and scope of the appended claims.

What is claimed is:

1. An isolated peptide comprising the amino acid sequence of SEQ ID NO:9, wherein the peptide further comprises an N-terminal group or a C-terminal group.

2. The peptide of claim 1 wherein the amino acid sequence consists of SEQ ID NO:9.

3. The peptide of claim 1 wherein the peptide consists of: (i) the amino acid sequence of SEQ ID NO:9; and (ii) an N-terminal group or a C-terminal group.

4. The peptide of claim 1, wherein the peptide comprises an N-terminal group and a C-terminal group.

5. The peptide of claim 1 wherein the peptide consists of the amino acid sequence of SEQ ID NO:9, an N-terminal group and a C-terminal group.

6. The peptide of any one of claims 1-3 wherein the N-terminal group is an amino group or an acetyl group.

7. The peptide of claim 6 wherein the N-terminal group is an acetyl group.

8. The peptide of any one of claims 1-3 wherein the C-terminal group is a carboxyl group or an amido group.

9. The peptide of claim 8 wherein the C-terminal group is an amido group.

10. The peptide of claim 5 wherein the N-terminal group is an amino group or an acetyl group.

11. The peptide of claim 10 wherein the N-terminal group is an acetyl group.

12. The peptide of claim 5 wherein the C-terminal group is a carboxyl group or an amido group.

13. The peptide of claim 12 wherein the C-terminal group is an amido group.

14. The peptide of claim 4 wherein the N-terminal group is an acetyl group and the C-terminal group is an amido group.

15. The peptide of claim 5 wherein the N-terminal group is an acetyl group and the C-terminal group is an amido group.

16. The peptide of claim 1, wherein the peptide is a dimer, trimer or a multimer.

17. A dimer, trimer or a multimer consisting of 2, 3 or more peptides, respectively, of the peptide of claim 2 or 3.

18. The peptide of claim 5, wherein the peptide is a dimer, trimer or a multimer.

19. The peptide of claim 15, wherein the peptide is a dimer, trimer or a multimer.

20. The peptide of claim 16, wherein the peptide is a trimer.

21. The peptide of claim 17, wherein the peptide is a trimer.

22. The peptide of claim 18, wherein the peptide is a trimer.

23. The peptide of claim 19, wherein the peptide is a trimer.

24. An isolated peptide comprising an amino acid sequence of SEQ ID NO:9, wherein the peptide is a dimer, trimer or a multimer.

25. The peptide of claim 1 or 2, which further comprises one or more reactive functionalities.

26. The peptide of claim 15, which further comprises one or more reactive functionalities.

27. The peptide of claim 1, wherein the peptide is up to 60 amino acids in length.

28. A composition comprising the peptide of any one of claims 1-3 or 5, and a pharmaceutically acceptable carrier.

29. A composition comprising the peptide of claim 15, and a pharmaceutically acceptable carrier.

30. A composition comprising the peptide of any one of claims 1-3 or 5, and a macromolecular carrier.

31. A composition comprising the peptide of claim 15, and a macromolecular carrier.

32. A composition comprising the peptide of any one of claims 1-3 or 5, a pharmaceutically acceptable carrier and a macromolecular carrier.

33. A composition comprising the peptide of claim 15, a pharmaceutically acceptable carrier and a macromolecular carrier.

34. The composition of claim 28 wherein said pharmaceutically acceptable carrier is water, buffered water, saline, 0.3% glycine, aqueous alcohols, or isotonic aqueous solution.

35. The composition of claim 29 wherein said pharmaceutically acceptable carrier is water, buffered water, saline, 0.3% glycine, aqueous alcohols, or isotonic aqueous solution.

36. The composition of claim 32 wherein said pharmaceutically acceptable carrier is water, buffered water, saline, 0.3% glycine, aqueous alcohols, or isotonic aqueous solution.

37. The composition of claim 33 wherein said pharmaceutically acceptable carrier is water, buffered water, saline, 0.3% glycine, aqueous alcohols, or isotonic aqueous solution.

38. The composition of claim 34, wherein the composition is sterile.

39. The composition of claim 35, wherein the composition is sterile.

40. A composition comprising a combination of antiviral agents for use in the treatment of HIV-1, the combination comprising: (i) the peptide of any one of claim 1-3 or 5; and (ii) one or more antiviral agents selected from the group consisting of an HIV entry inhibitor, HIV integrase inhibitor, reverse transcriptase inhibitor, protease inhibitor, vif-inhibitor, viral-specific transcription inhibitor, viral processing inhibitor, and HIV maturation inhibitor.

41. A composition comprising a combination of antiviral agents for use in the treatment of HIV-1, the combination comprising: (i) the peptide of claim 15; and (ii) one or more antiviral agents selected from the group consisting of an HIV entry inhibitor, HIV integrase inhibitor, reverse transcriptase inhibitor, protease inhibitor, vif-inhibitor, viral-specific transcription inhibitor, viral processing inhibitor, and HIV maturation inhibitor.

42. An isolated nucleic acid molecule comprising a nucleotide sequence encoding a peptide comprising the amino acid sequence of SEQ ID NO:9.

43. An isolated nucleic acid molecule comprising a nucleotide sequence encoding a peptide consisting of the amino acid sequence of SEQ ID NO:9.

44. A vector comprising the nucleic acid molecule of claim 42.

45. A vector comprising the nucleic acid molecule of claim 43.

46. The vector of claim 44 or 45, wherein the vector is an expression vector.

47. An isolated cell comprising the vector of claim 44.

48. An isolated cell comprising the vector of claim 45.

49. A method for inhibiting transmission of HIV to a cell, comprising contacting the virus, in the presence of a cell, with an amount of the peptide of any one of claims 1-3 or 5 effective to inhibit infection of the cell by HIV.

50. A method for inhibiting transmission of HIV to a cell, comprising contacting the virus, in the presence of a cell, with an amount of the peptide of claim 15 effective to inhibit infection of the cell by HIV.

51. The method of claim 49, further comprising administering one or more antiviral agents selected from the group consisting of an HIV entry inhibitor, HIV integrase inhibitor, reverse transcriptase inhibitor, protease inhibitor, vif-inhibitor, viral-specific transcription inhibitor, viral processing inhibitor, and HIV maturation inhibitor.

52. The method of claim 50, further comprising administering one or more antiviral agents selected from the group consisting of an HIV entry inhibitor, HIV integrase inhibitor, reverse transcriptase inhibitor, protease inhibitor, vif-inhibitor, viral-specific transcription inhibitor, viral processing inhibitor, and HIV maturation inhibitor.

53. A method for inhibiting HIV fusion, comprising contacting the virus, in the presence of a cell, with an amount of the peptide of any one of claims 1-3 or 5 effective to inhibit HIV fusion.

54. A method for inhibiting HIV fusion, comprising contacting the virus, in the presence of a cell, with an amount of the peptide of claim 15 effective to inhibit HIV fusion.

55. The method of claim 53, further comprising administering one or more antiviral agents selected from the group consisting of an HIV entry inhibitor, HIV integrase inhibitor, reverse transcriptase inhibitor, protease inhibitor, vif-inhibitor, viral-specific transcription inhibitor, viral processing inhibitor, and HIV maturation inhibitor.

56. The method of claim 54, further comprising administering one or more antiviral agents selected from the group consisting of an HIV entry inhibitor, HIV integrase inhibitor, reverse transcriptase inhibitor, protease inhibitor, vif-inhibitor, viral-specific transcription inhibitor, viral processing inhibitor, and HIV maturation inhibitor.

57. A method for treating an HIV-infected individual, comprising administering to the individual an amount of the peptide of any one of claims 1-3 or 5 effective to achieve, in the treated individual, a therapeutic result selected from the group consisting of: a reduction in the HIV viral load, an increase in circulating $CD4^+$ cell population, and a combination thereof.

58. A method for treating an HIV-infected individual, comprising administering to the individual an amount of the peptide of claim 15 effective to achieve, in the treated individual, a therapeutic result selected from the group consisting of: a reduction in the HIV viral load, an increase in circulating $CD4^+$ cell population, and a combination thereof.

59. The method of claim 57, further comprising administering one or more antiviral agents selected from the group consisting of an HIV entry inhibitor, HIV integrase inhibitor, reverse transcriptase inhibitor, protease inhibitor, vif-inhibitor, viral-specific transcription inhibitor, viral processing inhibitor, and HIV maturation inhibitor.

60. The method of claim 58, further comprising administering one or more antiviral agents selected from the group consisting of an HIV entry inhibitor, HIV integrase inhibitor, reverse transcriptase inhibitor, protease inhibitor, vif-inhibitor, viral-specific transcription inhibitor, viral processing inhibitor, and HIV maturation inhibitor.

61. A method for the treatment of HIV-1 comprising administering the peptide of any one of claims 1-3 or 5; and administering one or more antiviral agents selected from the group consisting of an HIV entry inhibitor, HIV integrase inhibitor, reverse transcriptase inhibitor, protease inhibitor, vif-inhibitor, viral-specific transcription inhibitor, viral processing inhibitor, and HIV maturation inhibitor.

62. A method for the treatment of HIV-1 comprising administering the peptide of claim 15; and administering one or more antiviral agents selected from the group consisting of an HIV entry inhibitor, HIV integrase inhibitor, reverse transcriptase inhibitor, protease inhibitor, vif-inhibitor, viral-specific transcription inhibitor, viral processing inhibitor, and HIV maturation inhibitor.

63. A method of synthesis of peptide comprising SEQ ID NO:9, said method comprises condensation of peptide fragments Fmoc-QQEKNEAALRE-OH and Ac-TTWEAWD-RAIAEYAARIEALLRALQE-OH, and further adding a leucine residue.

64. The method of claim 63, wherein the Fmoc-QQEKNEAALRE-OH is covalently coupled with a leucine amino acid residue at the C-terminal end prior to the condensation of the peptide fragments.

* * * * *